US010548549B2

(12) United States Patent
Boone et al.

(10) Patent No.: US 10,548,549 B2
(45) Date of Patent: Feb. 4, 2020

(54) MEASURING BREAST DENSITY USING BREAST COMPUTED TOMOGRAPHY

(71) Applicant: Regents of the University of California, Oakland, CA (US)

(72) Inventors: John M. Boone, Folsom, CA (US); Thomas R. Yellen-Nelson, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 246 days.

(21) Appl. No.: 15/669,829

(22) Filed: Aug. 4, 2017

(65) Prior Publication Data

US 2018/0008220 A1    Jan. 11, 2018

Related U.S. Application Data

(62) Division of application No. 11/913,494, filed as application No. PCT/US2006/017146 on May 3, 2006.

(60) Provisional application No. 60/677,704, filed on May 3, 2005.

(51) Int. Cl.
| A61B 6/04 | (2006.01) |
|---|---|
| A61B 6/00 | (2006.01) |
| A61B 6/03 | (2006.01) |
| A61B 8/08 | (2006.01) |
| A61B 8/00 | (2006.01) |
| A61B 6/12 | (2006.01) |

(52) U.S. Cl.
CPC .............. *A61B 6/482* (2013.01); *A61B 6/037* (2013.01); *A61B 6/0435* (2013.01); *A61B 6/4417* (2013.01); *A61B 6/502* (2013.01); *A61B 6/584* (2013.01); *A61B 8/0825* (2013.01); *A61B 8/4416* (2013.01); *A61B 6/03* (2013.01); *A61B 6/12* (2013.01); *A61B 6/405* (2013.01);

(Continued)

(58) Field of Classification Search
CPC ....... A61B 6/482; A61B 6/037; A61B 6/0435; A61B 6/4417; A61B 6/502; A61B 6/584; A61B 8/0825; A61B 8/4416; A61B 6/03; A61B 6/12; A61B 6/4208; A61B 6/405; A61B 6/5235

See application file for complete search history.

(56) References Cited

U.S. PATENT DOCUMENTS

| 5,024,229 A | 6/1991 | Bryant et al. |
|---|---|---|
| 5,912,720 A | 6/1999 | Berger et al. |
| 6,480,565 B1 | 11/2002 | Ning |

(Continued)

OTHER PUBLICATIONS

Kutluk et al., "Tissue density classification in mammographic images using local features," 2013 21st Signal Processing and Communications Applications Conference, 4 pages. (Year: 2013).*

(Continued)

*Primary Examiner* — Kiho Kim
(74) *Attorney, Agent, or Firm* — Kilpatrick Townsend and Stockton LLP

(57) ABSTRACT

A device and methods for performing a simulated CT biopsy on a region of interest on a patient. The device comprises a gantry (22) configured to mount an x-ray emitter (24) and CT detector (26) on opposing sides of the gantry, a motor (28) rotatably coupled to the gantry such that the gantry rotates horizontally about the region of interest, and a high resolution x-ray detector (172) positioned adjacent the CT detector in between the CT detector and the x-ray emitter.

41 Claims, 26 Drawing Sheets

(52) U.S. Cl.
CPC ........... *A61B 6/4028* (2013.01); *A61B 6/4423* (2013.01); *A61B 6/5235* (2013.01)

(56) References Cited

U.S. PATENT DOCUMENTS

| | | | |
|---|---|---|---|
| 6,560,311 B1 | 5/2003 | Shepard et al. | |
| 7,292,719 B2 | 11/2007 | Arnon | |
| 2002/0106055 A1 | 8/2002 | Cash | |
| 2002/0143249 A1 | 10/2002 | Tornai et al. | |
| 2006/0029268 A1* | 2/2006 | Endo | A61B 6/463 382/132 |
| 2006/0177125 A1 | 8/2006 | Chan et al. | |
| 2009/0006132 A1* | 1/2009 | Avinash | G16H 10/60 705/3 |
| 2012/0253187 A1* | 10/2012 | Hoernig | A61B 6/032 600/431 |

OTHER PUBLICATIONS

Benitez et al., "A quantitative analysis of breast densities using cone beam CT images", 2009, Proceedings of SPIE, vol. 7260, pp. 72602c-1 to 72602C-9. (Year: 2009).*

Bakic, et al., "Mammogram synthesis using a 30 simulation. I. Breast tissue model and image acquisition simulation" *Physics* vol. 29, pp. 2131-2139 (2002).

Samani, et al., "Biomechanical 3-D Finite Element Modeling of the Human Breast Using MRI Data" *IEEE Transactions on Medical Imaging* vol. 20, No. 4, pp. 271-279 (2001).

Tanner, et al., "A Method for the Comparison of Biomechanical Breast Models," *IEEE Workshop*, pp. 11-18, (2001).

Bar-Shalom, et al., "Clinical Performance of PET/CT in Evaluation of Cancer: Additional Value for Diagnostic Imaging and Patient Management," *Journal of Nuclear Medicine*, vol. 44, No. 8, pp. 1200-1209 (2003).

Yin, et al., "ImageParser: a tool for finite element generation from three-dimensional medical images," *BioMedical Engineering Online*, vol. 3(31), pp. 1-9 (2004).

Beyer, et al., "Acquisition Protocol Considerations for Combined PET/CT Imaging" *Journal of Nuclear Medicine* vol. 45, 25S-35S (2004).

Pathmanathan, et al.,"Predicting Tumour Location by Simulating Large Deformations of the Breast Using a 3D Finite Element Model and Nonlinear Elasticity" *Medical Image Computing and Computer-Assisted Intervention* vol. 3217, pp. 217-224 (2004).

PCT International Search Report for PCT/US06/17146, dated Nov. 21, 2006.

* cited by examiner

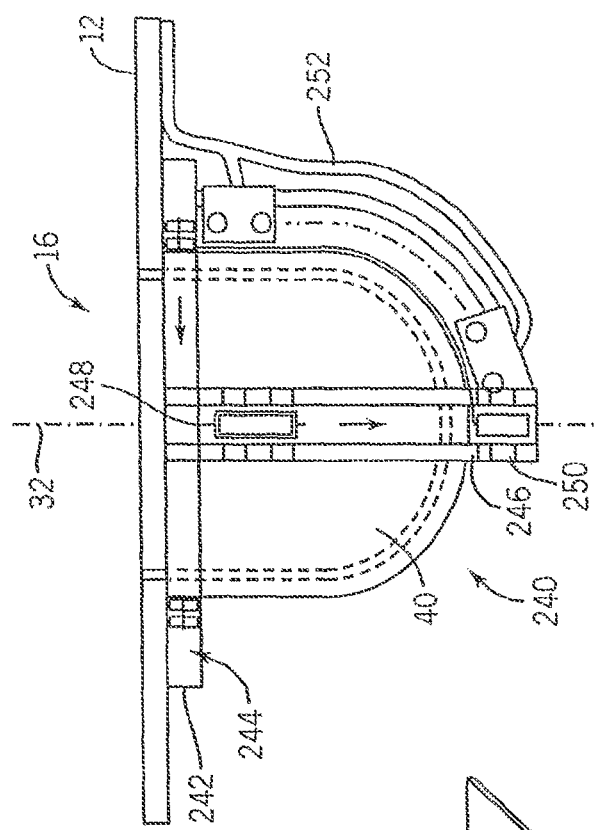
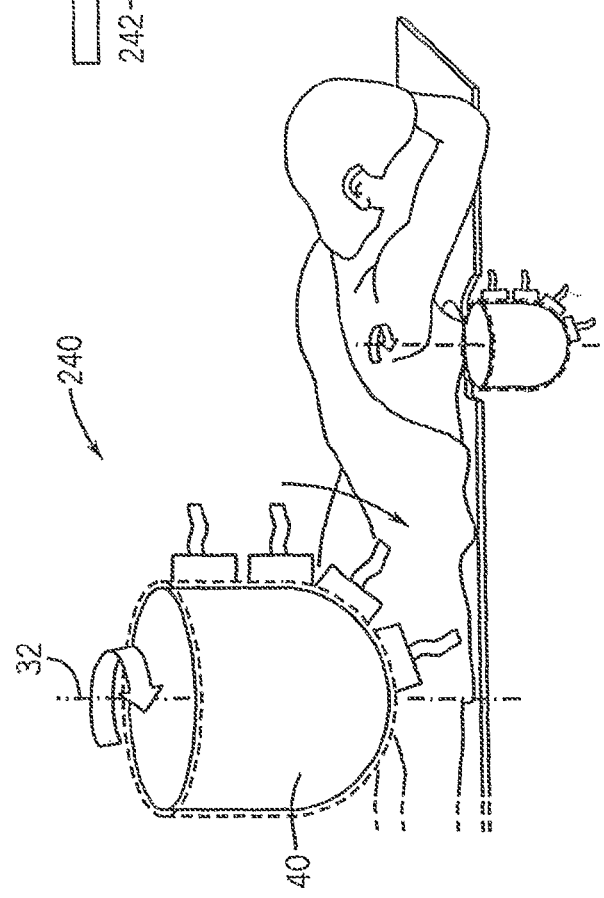
FIG. 23B
FIG. 23A

MEASURING BREAST DENSITY USING BREAST COMPUTED TOMOGRAPHY

CROSS-REFERENCE TO RELATED APPLICATIONS

This application is a divisional of U.S. application Ser. No. 11/913,494, filed Nov. 2, 2007, which is a U.S. National Stage Entry under § 371 of International Application PCT/US06/17146, filed May 3, 2006. Which is based on U.S. Provisional Application 62/677,704, filed May 3, 2005, hereby incorporated by reference.

STATEMENT REGARDING FEDERALLY-SPONSORED RESEARCH OR DEVELOPMENT

This invention was made with Government support under Grant Nos. EB002138 and EB89260, awarded by the National Institute of Health. The government has certain rights in this invention.

BACKGROUND OF THE INVENTION

1. Field of the Invention

This invention pertains generally to imaging of a patient's breast, and more particularly to improved methods and apparatus for breast diagnosis, evaluation and therapy through CT imaging.

2. Description of Related Art

X-ray mammography is used as the primary breast cancer screening test worldwide, and recent reports have suggested that mammography has been responsible for a sizeable reduction in breast cancer mortality. In standard mammography, the breast is generally compressed between two radiolucent plates of a compression fixture, and an x-ray image is taken through the plates and breast. The compression flattens the breast to decrease obscuring overlap of breast structure.

When suspicious lesions are found in mammography, a biopsy may be performed in which a needle is inserted into the breast tissue to obtain a sample of the tissue in the area of the lesion. In this case, the compression fixture can be used to stabilize the breast between the time of the image and the biopsy, guiding the biopsy needle in a manner that ensures its registration with the mammographic image.

Despite the important role that mammography plays in breast cancer screening, it is well recognized that mammography has limitations, particularly in women with dense breasts. The sensitivity of mammography averaged over the population is estimated to be approximately 75% to 85%, and models suggest that the sensitivity in dense breast is markedly lower. Further, even with compression of the breast, minor overlap of normal breast anatomy can sometimes obscure suspicious areas—especially in women with breast implants or very dense breasts. The compression can be uncomfortable and may deter some women from regular mammograms.

X-ray computed tomography (CT) allows the internal structure of tissue to be clearly imaged without the need to flatten or otherwise distort the tissue as is done in mammography. Nevertheless, standard whole-body CT is impractical for imaging the breasts because the axial scan used in such machines would deposit significant radiation in the torso and lungs near the breast. For this reason, specially designed CT machines have been proposed for imaging the breast ("breast CT machine") in which the scan is conducted in the coronal plane rather than axially. In such a system, the patient is positioned prone on a table. The table has openings in its surface admitting one or both breasts. A horizontally opposed detector and x-ray source rotate below the table about a vertical axis through the pendant breast. The smaller geometry of this machine can further provide improved image resolution.

One important benefit of a breast CT machine is that the breast need not be highly compressed as it is in conventional mammography. The reduction of compression needed to reduce the overlap of breast structure provides a more comfortable experience for the patient and can improve the imaging of some breast structure, such as breast ducts, which are unduly distorted by compression. One drawback to such breast CT machines, in instances where a suspicious lesion is found and a biopsy is required, is that compression of the breast in a standard mammography fixture and possibly re-imaging of the breast may be required to provide the necessary guidance for the biopsy procedure.

SUMMARY OF THE INVENTION

The present invention provides a set of tools that improves the ability to perform biopsies when using a breast CT machine. The invention allows the spatial coordinates of the suspicious lesions to be extracted directly from the breast CT images and these spatial coordinates to be used to guide a biopsy without repositioning or re-registration of the patient.

The invention first provides a multi-image display of breast CT data in any of several different formats: axial slices, coronal, sagittal and axial projections, volume rendered and/or virtual or actual compression mammograms. Each image may have a cursor that tracks with cursors in other images following a common position within the breast. The cursors allow accurate determination of the coordinates of the suspicious lesion as identified by a variety of methods including computer analysis of image/volume data and operator inspection of the images. As part of this process, an iterative matching system makes it possible to superimpose matching cursors, not only on the CT generated images, but on a standard mammogram taken earlier with a standard mammography machine.

Once the location of the suspicious lesion is identified, a robotic biopsy system incorporated into the CT system may provide a biopsy without the need to re-position the patient. Geometric correction of the CT machine using a specially designed phantom and/or the ability to image portions of the robot, before and during the insertion of the biopsy needle (using periodic updates of the breast image), allows an accurate biopsy on the same machine. The breast may be stabilized during this process with a support, for example, a suction collar having apertures for admitting a biopsy needle.

Alternatively, the present invention contemplates the possibility of a virtual biopsy on the same machine using a special high resolution CT detector that may focus in on the lesion to provide more detailed data. The small area of the detector provides rapid acquisition of data while limiting radiation exposure. Image artifacts normally produced when CT reconstruction is applied to truncated projection data that does not fully span the breast are avoided by using the earlier lower resolution data used to locate the lesion to supplement the high-resolution data.

The present invention also contemplates several novel measurements of the breast, including measurements and characterization of ductal architecture of the breast and measurements and characterization of breast density, the latter based on proportions of glandular tissue to non-glandular tissue. These measurements may provide for additional diagnostic information for the identification, detection, and treatment of breast cancer and long-term monitoring of longitudinal changes breast cancer.

More specifically, in one aspect of the invention, a simulated mammogram is created from CT data by employing an algorithm for compressing the volume data of the breast and projecting it into a two-dimensional image. A further aspect of the invention is employment of an algorithm to register the simulated mammogram to the patient's mammogram for identification of anatomic structures and suspicious areas. Iterating the compression algorithm with small changes in individual compression parameters (orientation, warping, scaling, shifting, elasticity, etc.) and comparing results, makes it is possible to (register) align the volume breast CT data to pre-existing mammography views. Further the algorithm may be employed to identify optimized views of suspicious areas for the improving compression mammogram projection images.

The aligned breast image data can then be displayed side-by-side, permitting the mammographer to compare both sets of images. Additionally, once the compression parameters are known, it is possible to co-locate lesions, suspicious findings, or other structures in one set of images and have the compression algorithm depict the location in the other images and volume data.

In a further aspect of the invention, CT volume data is used to accurately guide needle-core biopsy using computer-controlled robotic technology. Using this approach, the woman's breast is scanned using the breast CT scanner. The radiologist or other physician then localizes the site of suspicion in the volume data set using various image display techniques. From this data, computer algorithms guide the movement of a motion-enabled robotic arm for the placement of the needle biopsy gun or a guide into the optimal position so that the biopsy "gun" is accurately positioned for biopsy. The physician then activates the spring-loaded biopsy gun to inject the needle to the site of the suspicious lesion. Alternatively, the computer can drive the needle to the suspected lesion under image-guided control. The CT scanner and targeting algorithm can be employed to provide periodic updates of the breast image data to refine the trajectory or path of the biopsy device optimizing accurate sampling of the target lesion.

In another aspect of the invention, a method of computing a physiological characteristic of a target tissue in a patient's breast identifies glandular tissue and provides a breast density measurement based on relative proportion of glandular tissue in the breast. The breast density value may provide an indication of risk of breast cancer.

Yet another aspect of the invention may provide a simulated CT biopsy of a region of interest on a patient using a separate high-resolution x-ray detector augmenting the standard detector and the x-ray emitter. A plurality of actuators may be coupled to the gantry to move the collimators and high-resolution detector in a sinusoidal pattern while the gantry rotates to keep it focused on a possible lesion to provide a high-resolution image of the lesion.

A further aspect of the invention is an apparatus for performing a biopsy on a region of interest of the patient. The apparatus comprises a gantry configured to mount an x-ray emitter and a CT detector on opposing sides of the gantry, a motor rotatably coupled to the gantry such that the gantry rotates horizontally about the region of interest to generate CT images of the region of interest, and a robotic arm configured to house a biopsy needle, wherein the robotic arm is further configured to position the needle at the location of interest based on the CT images of the region of interest.

A further aspect is a device for immobilizing breast tissue by stabilizing a smaller region of interest on the breast. A method is also disclosed whereby the tissue is stabilized with a vacuum device that firmly holds the tissue without compression. An advantage of the current method is that it operates only over a defined region, the size of which can be modified by using different applicators. The method further employs vacuum stabilization such that tissue is most firmly stabilized at the areas of contact of the applicator and the lines of force are in opposition to force lines for any interventional device appliance, minimizing tissue displacement during procedures. As a result, the method provides optimal force management while minimizing tissue stress. The depth of the stabilization can be increased through use of larger applicators. Larger tissue regions may also be stabilized with augmentation via external compression plates or additional applicators.

Another aspect of the invention is an apparatus for generating the image of a region of interest of a patient. The apparatus has a gantry configured to mount an x-ray emitter and a CT detector on opposing sides of the gantry, a motor rotatably coupled to the gantry such that the gantry rotates horizontally about the region of interest to generate CT images of the region of interest, and a PET detector coupled to the gantry to generate PET images of the region of interest substantially simultaneous with the CT images.

Another aspect of the invention is an apparatus for generating the image of a region of interest of a patient. The apparatus has a gantry configured to mount an x-ray emitter and a CT detector on opposing sides of the gantry, a motor rotatably coupled to the gantry such that the gantry rotates horizontally about the region of interest to generate CT images of the region of interest, and an ultrasound scanner coupled to the gantry to generate ultrasound images of the region of interest substantially simultaneous with the CT images.

A further aspect of the invention is a method for generating the projection image of a region of interest of a patient. The method includes the steps of injecting a contrast agent into the region of interest, emitting x-rays through the region of interest, and acquiring projection image data sets from a detector configured to detect the emitted x-rays passing through the region of interest.

A further aspect of the invention is a method for using a contrast material and generating the CT images from the breast or a region of interest within the patient. The method includes the steps of injecting a contrast agent that arrives at the region of interest, emitting x-rays through the region of interest, and acquiring CT image data sets from a detector configured to detect the emitted x-rays passing through the region of interest. Subsequently, CT images of the region of interest are produced demonstrating the lesion.

In one embodiment of the current invention, acquiring projection image data sets includes the steps of acquiring data from a low energy emission, acquiring data from a high energy emission, and obtaining a dual energy subtraction image from the acquired data. The dual energy subtraction can be used with the injection of contrast agent to enhance its appearance.

A further aspect of the invention is a method of calibrating a CT scanner by placing one or more objects having known dimensions and material properties in the field of view of the scanner, tracking the location of the one or more objects with a tracking algorithm, and using the paths of the one or more objects to calibrate the CT scanner.

In yet another aspect of the present invention, a graphic user interface (GUI) for displaying CT images is disclosed. The GUI comprises simultaneous display of two or more views of the CT image, wherein the two or more views depict planar or rendered views at different angular orientations from one another such that rotation of the image in the first view results in a corresponding rotation of the image in the other views. The GUI may also include alignment lines connecting a region of interest in the CT image in the first view to the corresponding location of the region of interest in the second view. The GUI provides a cursor to designate locations of interest. Coordinates are then generated that are used by an algorithm to provide a trajectory for the biopsy devise and optimize that trajectory. In some situations updated image (CT, US, etc.) image information will be used to monitor and refine the trajectory.

Yet a further aspect of the invention is a method of determining abnormal structures in a patient's breast. The method includes the steps of generating CT images of a series of reference patients, identifying normal duct structures in the generated CT images to generate a database of normal duct structures, generating CT images of a patient to be diagnosed, and comparing the CT images of the patient to be diagnosed with the database to identify an abnormal structure in the patient's breast.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIGS. 23A and 23B are schematic views of an alternative robotic assembly of the apparatus of FIG. 21.

DETAILED DESCRIPTION OF THE INVENTION

Referring more specifically to the drawings for illustrative purposes, the present invention is embodied in the apparatus generally shown in FIG. 1 through FIG. 37. It will be appreciated that the apparatus may vary as to configuration and as to details of the parts, and that the method may vary as to the specific steps and sequence, without departing from the basic concepts as disclosed herein.

1. CT Imaging of Pendant Breast.

Figure 1:
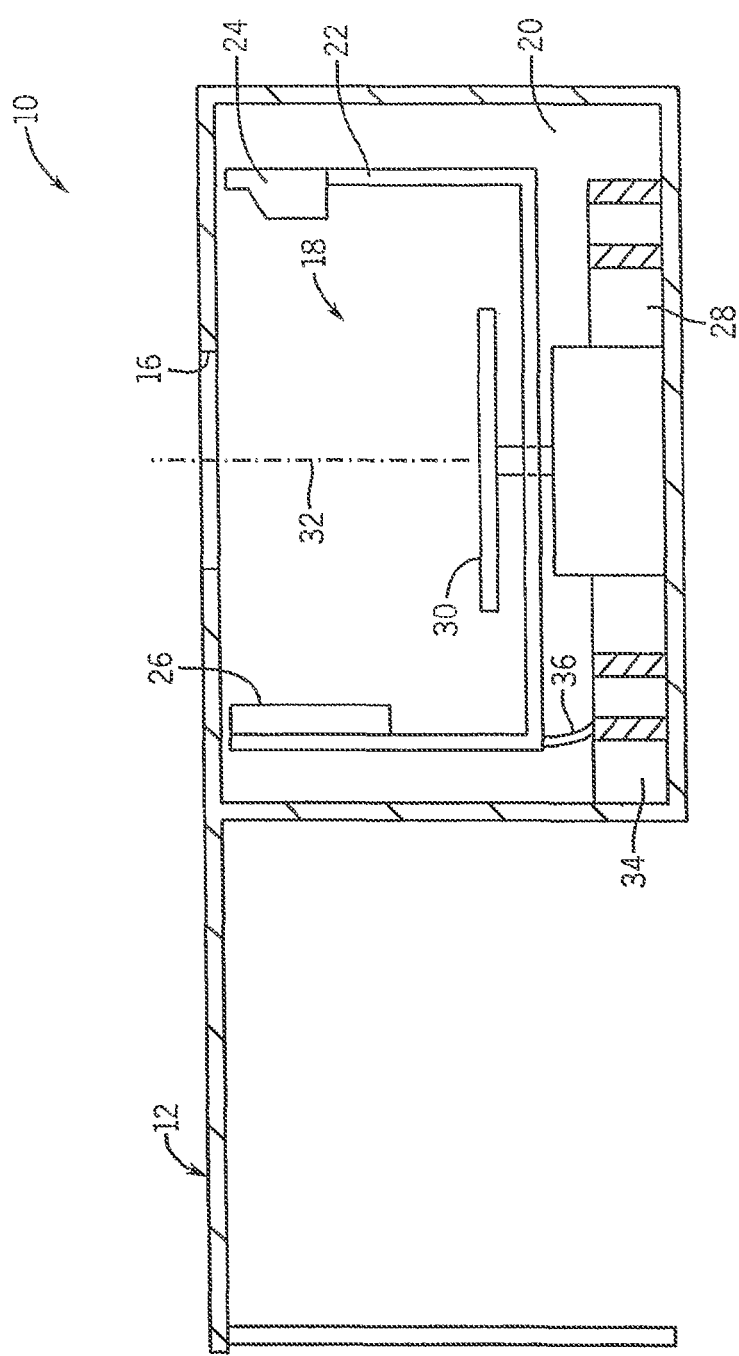
FIG. 1 is side view of a horizontal CT breast scanner of the present invention.

Referring to FIG. 1, a breast CT scanner 10 tailored specifically for breast cancer screening is shown. The scanner has a padded table 12 with a circular opening 16 through which the patient may individually position the breast to be screened. A CT scanning mechanism 18 is positioned in chamber 20 under the table 12. The scanning mechanism 18 comprises an x-ray emitter 24 and detector 26 supported on opposing sides of a rotating gantry 22. A centrally located motor 28 is mechanically coupled to the gantry 22 so that the gantry 22 is rotated in the horizontal plane about axis 32 during operation. A chain link conduit provides a flexible spiral linkage for cables 36 connected to the gantry 22 and x-ray emitter 24 and detector 26.

Figure 2A:
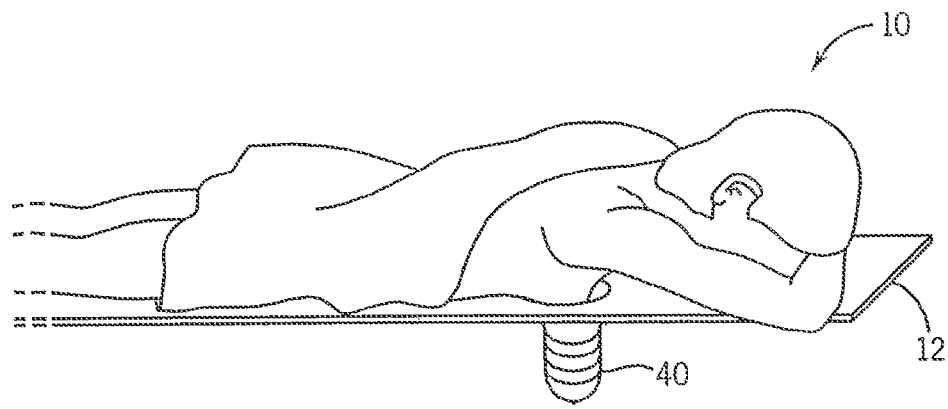
FIG. 2A is a perspective view of a patient with breast positioned in the scanner of FIG. 1.
Figure 2B:
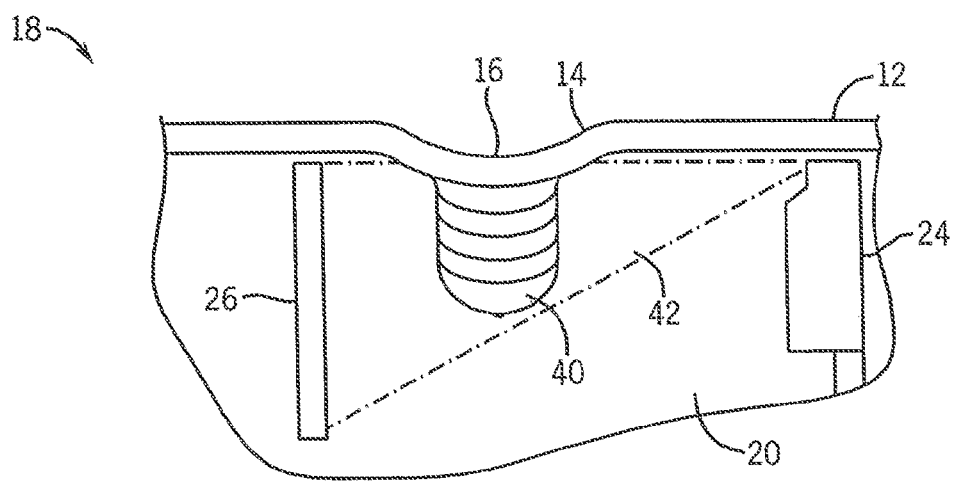
FIG. 2B is a side view of a patient with breast positioned in the scanner of the present invention.

FIGS. 2A and 2B illustrate the CT scanner 10 of the present invention being used to capture CT images of a patient's breast 40. With the patient lying prone on the table 12, the patient's breast 40 hangs in a pendant position though opening 16 in depression 14 into chamber 20. The gantry 22 rotates 360 degrees about the pendent breast 40, while the scanning mechanism 18 continually registers images as the x-ray beam 42 emitted from emitter 24 passes through the tissue of breast 40. The scanning mechanism 18 images at a rate of 30 frames per second, but may also image at faster or slower rates to accommodate the capture rate of the detector. The process takes about 17 seconds per breast to complete, but may vary to increase the number of captured images or lessen the amount of time the patient is required to remain still.

Figure 28:
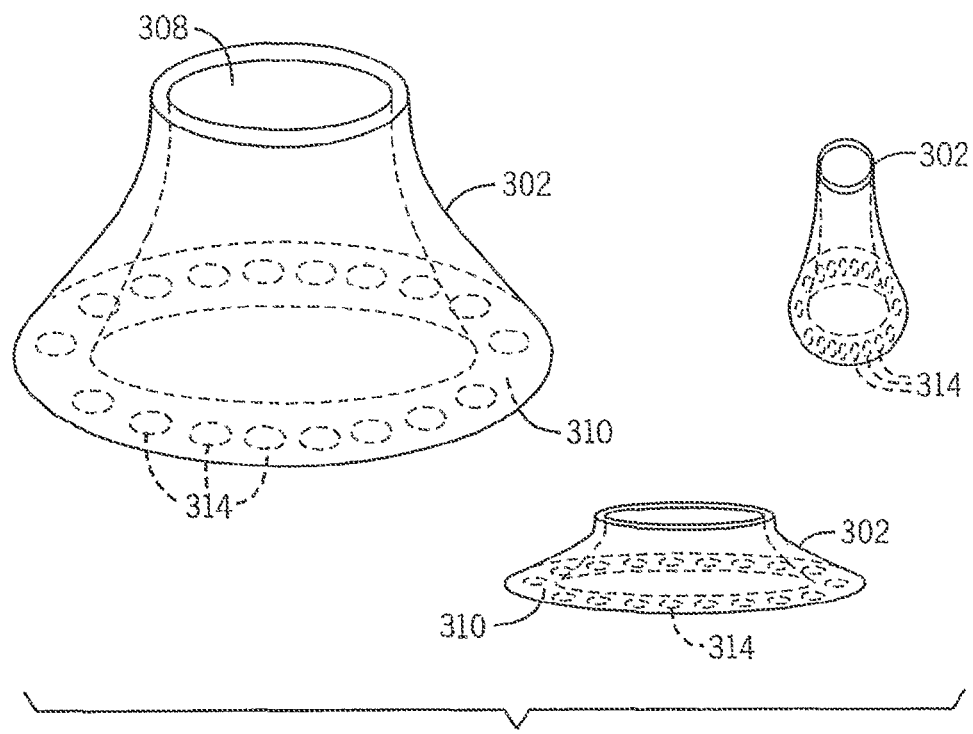

No breast compression is necessary when imaging with the breast CT scanner 10, and the radiation levels are substantially equivalent to levels generated in typical mammography. The horizontal orientation of the scanner 10 also prevents the exposure of tissues in the thoracic cavity, because the CT is performed in the coronal plane. To ensure that breast tissues close to the chest wall and in the axilla are imaged, the x-ray emitter 24 and detector 26 are positioned just below the bottom of the shielded table 12. The table surface surrounding the opening 16 for the breast comprises a depression 14 or swale to allow a portion of the chest wall to extend into the scanner field of view defined by beam 42 and thus enable adequate coverage of the breast 40, as shown in FIG. 28. Gentle pressure beyond gravity would be applied to immobilize the breast 40 and pull the breast tissue away from the chest wall, but the breast compression used in mammography would not be necessary.

The coronal acquisition geometry of the dedicated breast CT scanner 10 would allow the reconstructed CT images to be sized to the dimensions of the breast. For example, for a 15-cm-diameter field of view defined by the beam 42, a 512×512 CT image would have pixel dimensions close to 300 µm These dimensions may be manipulated according to the trade-off between image noise and voxel volume. Isotropic resolution (e.g., 300 mm×300 mm×300-µm voxels), however, might be useful in concert with three-dimensional viewing techniques and could be achieved by using cone beam techniques with flat panel detectors. For routine breast CT scanning, the section thickness probably would be on the order of 1-2 mm.

The scanner 10 illustrated in FIG. 1 may also be used to image other anatomical areas of interest of a patient. For example, the opening 16 may be sized so that the patient may stand on the platform 30 to image a portion of the patient's leg. The platform 30 remains stationary while the gantry 22 rotates during imaging. This may be particularly useful in capturing CT images of a patient's knee under normal loading while standing.

2. Simulated Breast Compression.

Figure 3:
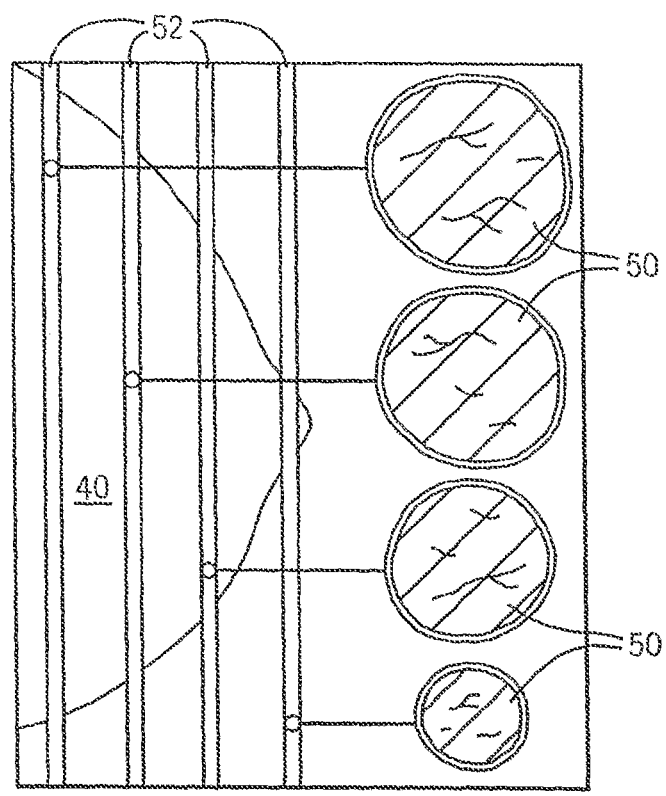
FIG. 3 is a series of CT images taken at various coronal sections along a patient's breast.

The breast CT scanner, such as that shown in FIGS. 1, 2A and 2B, produces about 300 individual images per breast. Referring now to FIG. 3, each image is a virtual coronal slice 50 through the breast 40. As seen in FIG. 3, each of the vertical lines 52 indicates the area of the breast 40 where each slice 50 was taken. In contrast, standard compression mammograms are X-rays taken through all layers of the breast via a projection imaging procedure utilizing relatively aggressive physical compression of the breast. Because most radiologists currently diagnose breast cancer using mammography, they are accustomed to and trained at viewing breast images which are mechanically compressed. Therefore, in order to compare the breast CT images with the more conventional mammography images, it is desirable to present the images in the fashion with which radiologists are familiar.

Figure 4:
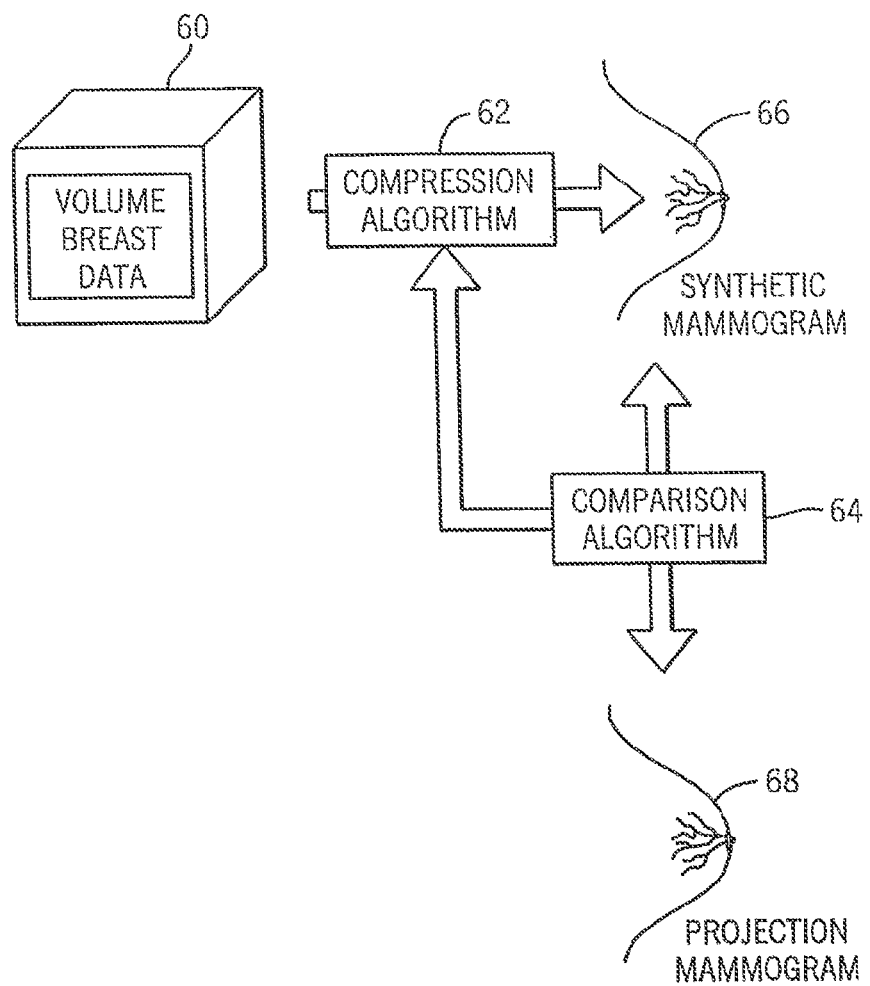
FIG. 4 is a schematic view illustrating an apparatus for simulating mammogram compression of breast tissue using uncompressed CT volume datasets.

Now turning to FIG. 4, a preferred method of the present invention uses a mathematical compression algorithm 62 to transform the three-dimensional volume data set 60 generated from a breast CT scanner into a compressed three-dimensional version simulating compression of a breast in a standard compression mammography image where the breast is compressed between two parallel and opposed compression plates. The compressed volume breast data 60 is then projected onto a two-dimensional image, or synthetic mammogram 66. The synthetic mammogram 66 is then compared to an actual standard compression mammogram 68 from object (e.g., Mediolateral Oblique View (MLO) or the Cranio-Caudal View (CC) compression mammograms) via comparison algorithm 64. Based on defined goodness-of-match criteria, the comparison algorithm 64 will adjust a first of a plurality of parameters, repeat the projection process to generate a new synthetic mammogram 66, and then re-apply the comparison algorithm 64. This process continues until the goodness-of-fit criteria are met, wherein the algorithm saves the compression parameters and presents the images to the observer for comparison against the original projection images. This process is repeated for each original projection image resulting in a series of compression parameters for each projection image to volume projection.

Figure 5:
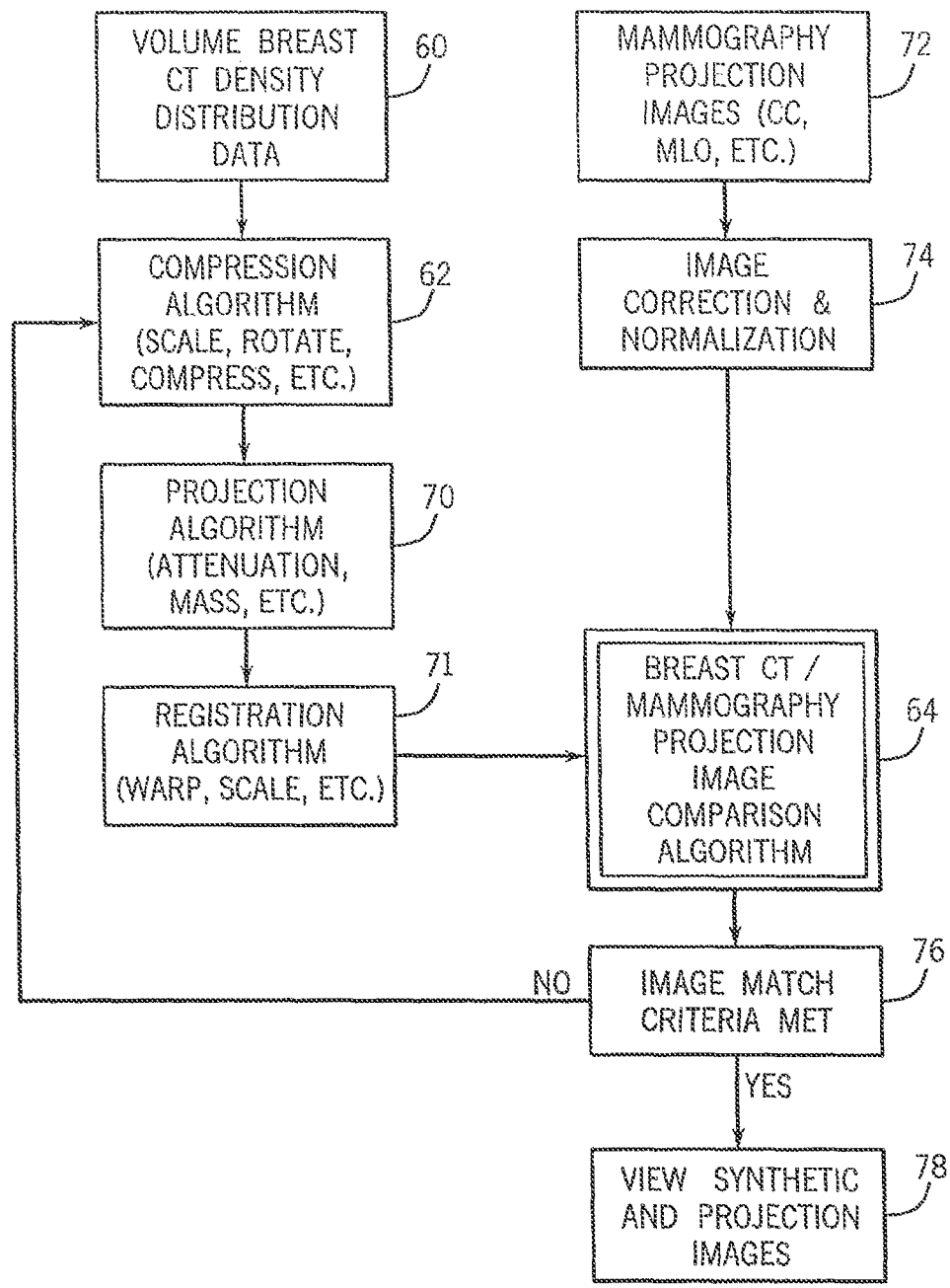
FIG. 5 is preferred method of the present invention using a mathematical compression algorithm to transform the three-dimensional volume data set generated from a breast CT scanner.

A more detailed view of the method of the present invention is shown in FIG. 5. The compression algorithm 62 takes the volume data 60 and compresses it, determining compression parameters for the compression which simulate actual physical compression of the breast during mammography (either by mechanical modeling of the breast or by a simple geometric distortion).

In the preferred embodiment, compression algorithm 62 incorporates breast tissue elasticity values to better simulate actual mammography compression. Breast tissue elasticity may be further determined from compression and registration. Compression algorithms may also be based on mathematical compression models and image registration models, or other methods incorporating physical and image parameters of volume breast CT and projection radiographs.

After compression, the data is projected onto a two-dimension image plane via a projection algorithm at step 70 to simulate an x-ray mammogram and the resulting synthesized mammogram is registered to an actual mammogram at process block 71. The registration algorithm 62 may employ techniques including, but not limited to, one or more of the following commonly used in the art: scaling, rotation, shifting, shearing and non-linear warping.

The synthesized and registered mammogram from process block 71 is then compared to the actual mammogram at process block 64. Prior to comparison, the mammography projection images 72 may be corrected and normalized at step 74. The comparison may be made on the basis of image information, such as the correlation of coefficient, energy, entropy or other similar methods commonly used in the art.

After the comparison algorithm 64, image match criteria are applied at 76. If the image match criteria are met, the synthetic and mammography projection images are displayed at 78. If the image match criteria are not met, the compression algorithm 62 is reapplied with at least one of the compression parameters and/or registration parameters being varied.

Figure 6:
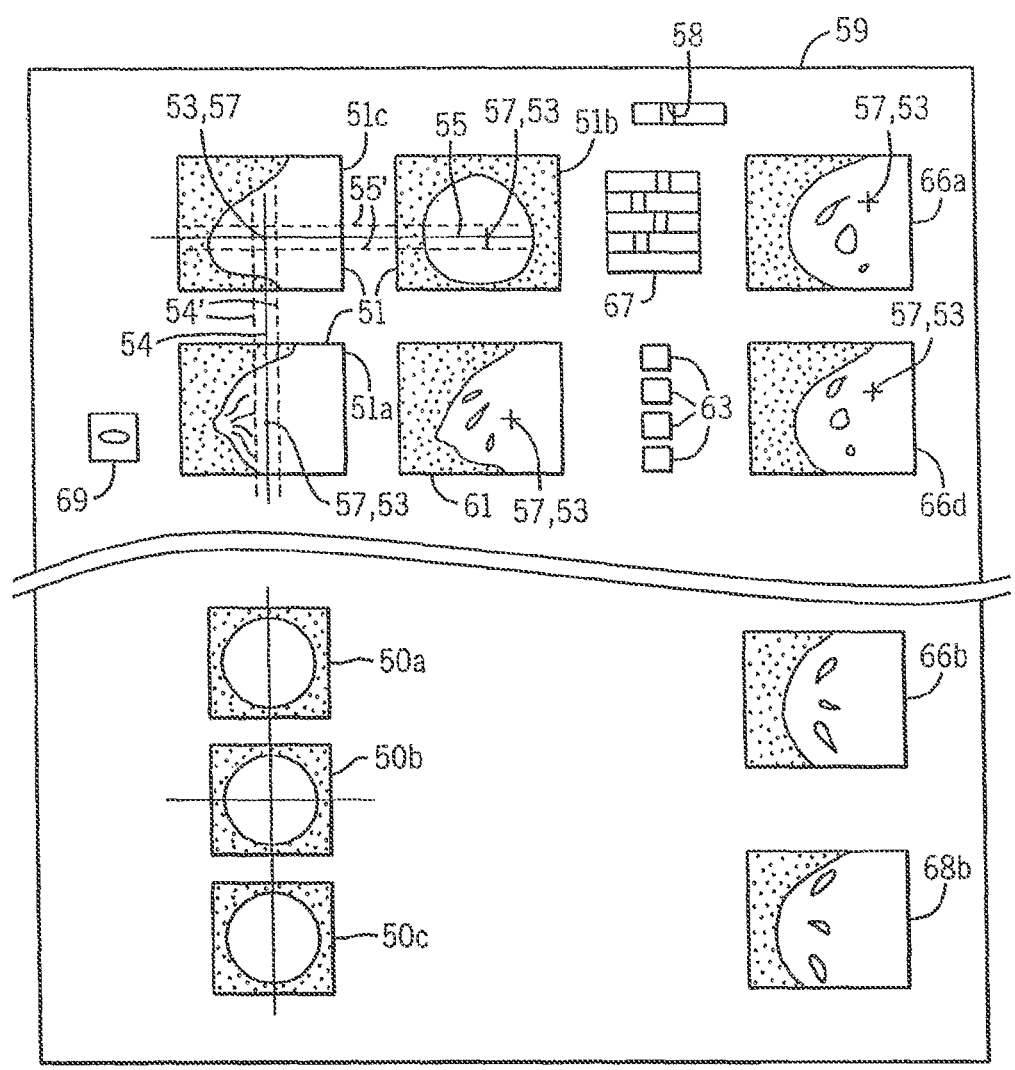
FIG. 6 is a view of a display provided to a user of the CT allowing multiple image representations linked by a common cursor.
Figure 7:
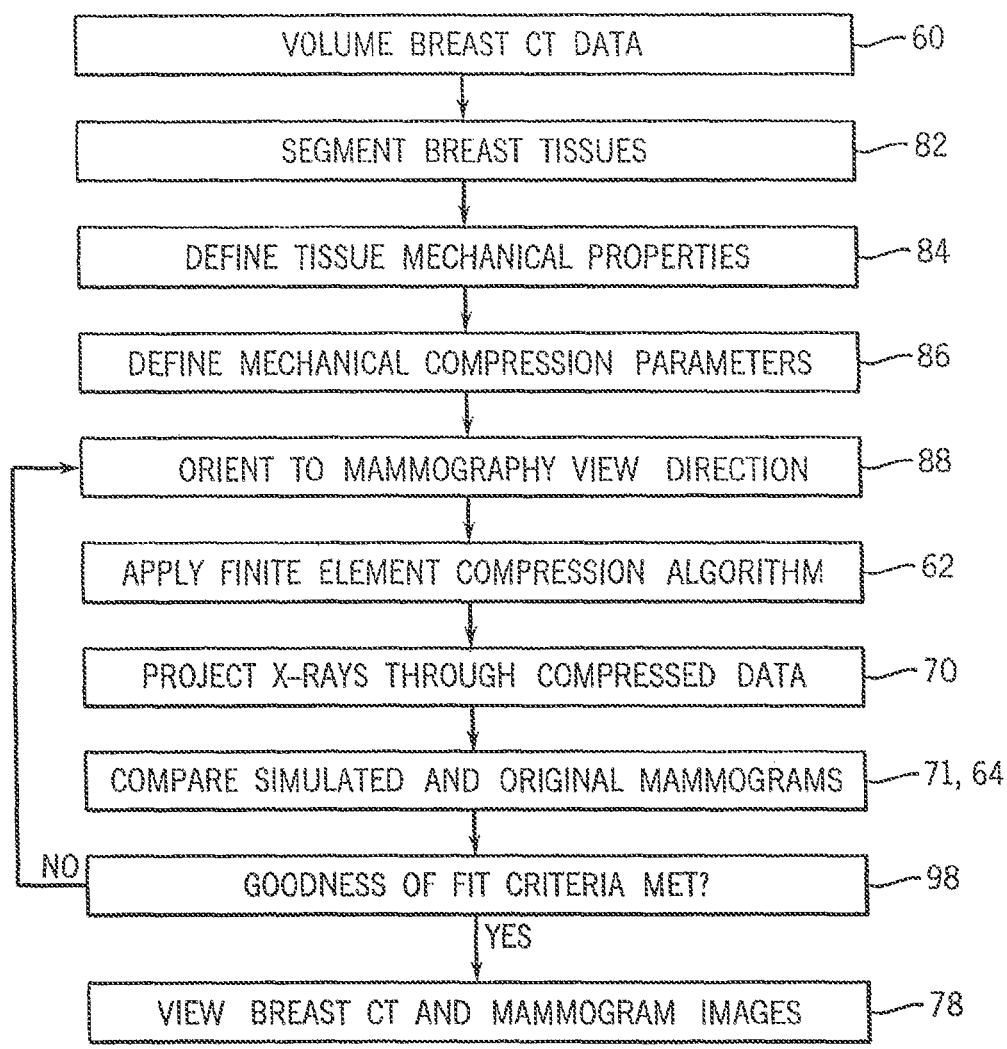
FIG. 7 is a detailed flow diagram of the compression algorithm of the present invention.

Referring now to FIG. 7, a compression algorithm 62 making use of an understanding of the physical structure of the breast is illustrated in more detail. The volume data is first acquired in a volume imaging system (e.g., breast CT scanner) at step 80. The volume data may be pre-processed to stabilize and standardize the data. Concurrently or previously acquired projection images (e.g., CC and MLO views from conventional mammography) are used for comparison, as shown in FIG. 6. In the present embodiment, the number of projection images employed is flexible and does not alter the basic functionality of the algorithm.

To assure proper operation of the algorithm, the data may be oriented to a standard orientation (e.g., nipple down, to the right, etc. with the breast base at the top, left, etc.) The different types of breast tissue (e.g., skin, fat, glands, tumor, etc) are then segregated for example by use of a histogram of the data and morphological filters (such as erosion) described herein. At process block 84 and 86, empirically derived mechanical and compression properties are then assigned to each of these tissue types and a model of the breast is constructed, for example using finite element techniques.

At process block 88 the data is oriented with respect to the actual mammogram to which the data will be compared and at process block 90 a virtual compression of the finite element model is applied.

Volume data are then projected in the direction of the z-axis onto an image plane at 70 by summation along the projection path of each voxel in the volume data set as distorted by the displaced locations of the elements of the compressed finite element model. Summation of the voxels is determined by the voxel value (i.e., density, etc.) and a summation integral that may evaluate the attenuation (e.g., x-ray, optical, etc.), transparency, or some other parameter to arrive at the projected value along the ray.

The algorithm may further transform the contrast properties of the volume data to better match the projection contrast properties of the mammography projection images 72. For example, the CT data set acquired at relatively high kVp (x-ray beam energies) may be transformed to simulate the low x-ray beam energies exemplary of mammography scans. With the known composition of each voxel in the three-dimensional volume data set, linear attenuation coefficients at the lower x-ray energies representative of mammography may be used.

Coordinate alignment can be performed between volume projection and mammogram(s) to co-locate lesions in both data sets, either a lesion seen in a mammogram to a position in volume, or a lesion seen in volume to a position in a mammogram.

Referring still to FIG. 7, the resultant projected image from step 70 is then registered at step 71 and compared to the projection image based on one or more of a plurality of parameters at step 64 (e.g., difference error, correlation coefficient, mutual information, entropy, etc.). If the images match within the specified criteria, the algorithm proceeds to step 78 and the image is displayed. Once the extent of compression to match images is obtained, the elastic parameters for each voxel are updated to those calculated by the compression algorithm. Other means of determining compression commonly used in the art may also be employed to accomplish this part of the algorithm.

If the images do not meet the specified criteria, the algorithm iterates by making a small adjustment in one of the compression or orientation parameters and repeats the process. This process continues until the specified criteria are met. In a purely geometric implementation of the compression algorithm, compression in the form of a geometric warp is applied in the base direction. If fit criteria are not met at step 98, the compression is varied until the fit criteria are met. Each remaining Z level is optimally warped until the entire compressed volume projection matches the conventional projection image. The process is repeated for each conventional projection view. Once completed, the final compression parameters are saved for viewing at step 78. The mathematical compression techniques of step 62 may take the form of affine transforms, or any number of other mathematical algorithms which can (linearly or nonlinearly) mathematically distort the breast from the uncompressed (x, y, z) to the compressed (x', y', z') format.

In both types of compression, the compression parameters are saved as both a forward and backward set that fully characterizes the relationship between the volume data and the projection data.

Referring now to FIG. 6, the present invention may display the CT acquired volume data in a variety of forms. In one embodiment, a three-view orthogonal display 51 provides a simultaneous presentation of an axial image 51a, a coronal image 51b, and a sagittal image 51c, each of which provide a user selected slice of data along the associated coronal, sagittal and axial planes. In addition a volume rendered image 61 in any of these planes (sagittal shown) may be provided that combines data of the volume data from many slices or from a single slice of variable thickness to produce a simulated radiographic projection through the uncompressed breast. The data of the volume rendered image 61 may be subject to a different weighting systems as selected by the user including a simple summation of the data along the rays of projection or a selection of the maximum value of data along the projection, etc.

As shown, the axial image 51a, coronal image 51b, and a sagittal image 51c may be optionally aligned each to share one image axis, for example, with the axial image 51a positioned above the coronal image 51b, and the sagittal image 51c positioned to the right of the coronal image 51b. In this way, a given location 53, having a unique x, y and z coordinate within the volume data of the breast, can be highlighted with a cursor 57 on each of the orthogonal axial image 51a, a coronal image 51b, and a sagittal image 51c. An optional vertical alignment line 54 connecting the locations 53 in axial image 51a and sagittal image 51c (showing the plane of the slice of the coronal image 51b), and an optional horizontal alignment line 55 connecting the locations 53 in the coronal image 51b and the sagittal image 51c (showing the plane of the slice of the sagittal image 51c) can also provided, each line 54 and 55 flanked by parallel lines 54' and 55' respectively showing the thickness of the given slices.

In addition, a synthetic mammogram 66a may be presented showing the sagittal view of the breast with virtual compression, as described above, to simulate an actual mammogram 68a, which may also be displayed. A cursor 57 may also be marked on the synthetic mammogram 66a corresponding to locations 53 in the axial image 51a, coronal image 51b, and the sagittal image 51c using the mapping described by the forward and backward set characterizing the relationship between the CT volume data and the projection data described above. A similar cursor 57 can be placed in the same location on an actual sagittal mammogram 68a previously acquired on a separate mammography machine and based on the matching done between the synthetic mammogram 66a and the actual mammogram 68a, as described above.

In addition to synthetic mammogram 66a in the sagittal plane, an axial plane synthetic mammogram 66b may be provided and optionally matched to an axial compression mammogram 68b previously acquired on a separate mammography machine. In addition, multiple coronal slice images, for example, slices 50a, 50b, and 50c may be provided and, in each of these images, corresponding cursors 57 located to move with the cursors 57 in the other images. Each of the images may be moved and rotated with corresponding movements and rotations being automatically effected in the other images.

By allowing the cursors 57 to move in tandem under the guidance of an operator, the same location 53 may be pinpointed in all displayed images and a simultaneous computation and optional display of actual coordinates 58 of the location 53 may be provided as can be used in guiding a virtual or actual biopsy. This common interactive cursor 57 allows the operator to co-locate lesions and other structures present in any of the images to the location of all other images. Since radiologists typically only have experience in viewing breast images in this compressed projection imaging format, it is highly desirable to develop this viewing technique for radiologists to learn and make use of breast CT images.

Each of the images can be freely manipulated on the display 59 as individual windows per conventional techniques and arranged for the convenience of the operator. Lightness, contrast, magnification and orientation of each of the images may be freely adjusted and conventional tools allowing for measurement of areas, lengths, and volumes on the images may be provided according to techniques well known in the art. These tools may also provide for histograms or other analysis of the underlying data of the images within regions selected by the operator. Thus a lesion can be identified using not only visual inspection of the images but also by computer analysis of image/volume data with respect to density, geometry, roughness, architecture, and more, as guided by the user.

The display 59 may further provide a set of user manipulatable controls 67 allowing control of the location of the cursors 57 (or direct control of the cursor 57 by dragging the cursor on any image), an amount of magnification of the image, and the thicknesses of the slice of data from which the volume rendered image 61 is created. Given images may be stored and accessed by "snapshot" icons 63 storing the image parameters and pointing to the correct data so as to allow that image to be recreated and yet further manipulated. For slice images, the slice may change as the cursor location is moved, so that a slice holding the cursor is always displayed.

A region of interest control 69 allows creation of a region of interest within the displayed data generally defining a bounded volume around the cursor 57 and that data to be individually viewed and manipulated. This tool allows isolation of the volume data related to the lesion to provide a virtual "electronic scalpel". By removing this region from the image, or by removing image data surrounding the region, the region may be better examined. The region and non region data may be processed differently to accentuate these differences. Further, the underlying data as segregated may be quantitatively processed to characterize the tissue to the operator.

The image manipulation and fitting technique described above, which allows matching of mammography data to the tomographic data, can also be used to match tomographic or mammographic data taken over time in, for example, a longitudinal study. Using the compression parameters used in generating the synthetic mammogram, the operator can co-locate lesions or other structures present in the mammogram in all other images. Since radiologists typically only have experience in viewing breast images in this compressed projection imaging format, it is highly desirable to develop this viewing technique for radiologists to learn to make use of breast CT images.

3. Breast Density Evaluation, Risk Prediction, and Personal Screening.

Breast density refers to the amount of glandular tissue in a woman's breast, and typically younger women have higher degrees of glandularity, with glandularity becoming reduced in postmenopausal women. It has been demonstrated by other researchers that women with higher breast density (increased breast glandular component) have a higher probability of getting breast cancer. Thus, in routine breast CT scanning, the evaluation of breast density can be used as a measure of subsequent risk, and could in fact be used to tailor individualized risk-based screening approaches for each individual woman. In mammography, assessment of the fraction of the breast that is glandular is difficult because the tissues are all superimposed onto each other.

Breast CT, by virtue of the fact that the volume data set of images eliminates overlapping tissues, enables the direct calculation of breast density. Automatic algorithms are used to produce accurate measurements of breast density from the breast CT volume data set, and these measurements could play an important role in the medical and risk management of individual women.

Figure 8:
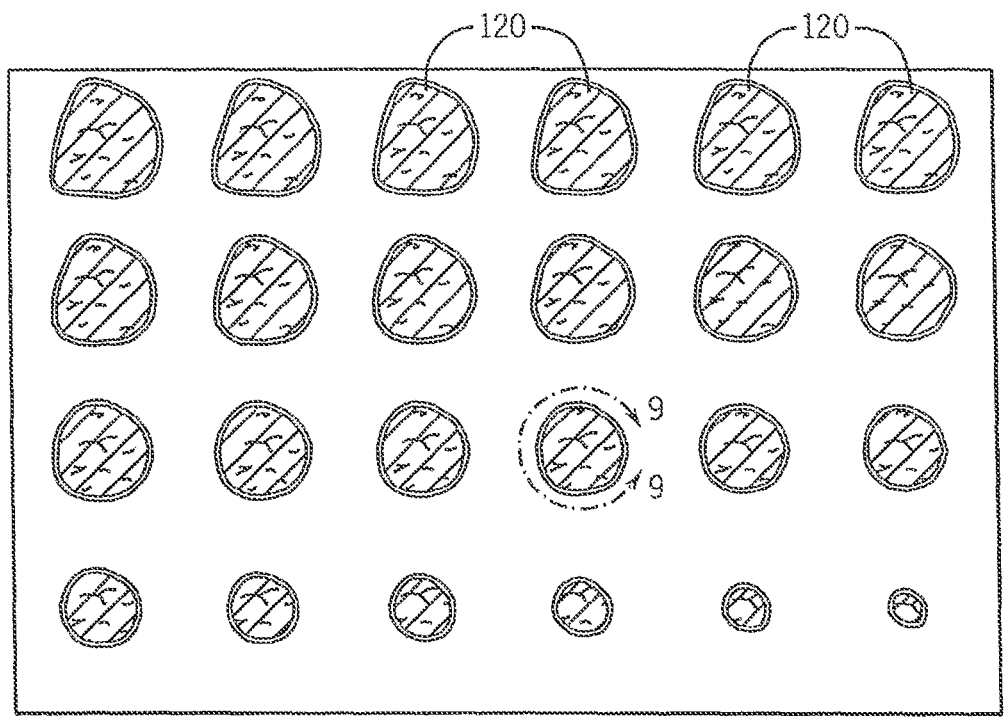
FIG. 8 is a series of coronal CT views of a patient's breast.
Figure 9:
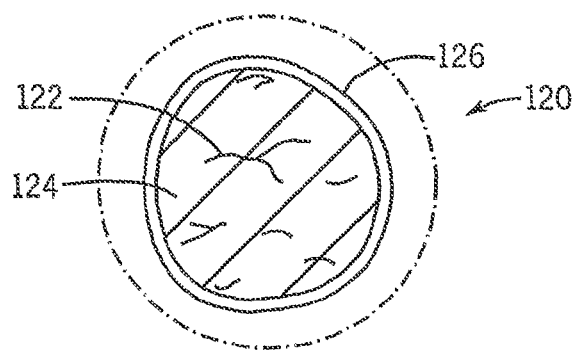
FIG. 9 is an expanded view of one of the coronal views of FIG. 8.

FIG. 8 illustrates a sample of twenty-four breast CT images 120 out of the approximately 300 images produced by typical breast CT of one breast. The breast images 120 demonstrate coronal views of the breast from the base of the breast (upper left) to the nipple (lower right). FIG. 9 shows an exploded view of one of the images 120 which generally comprises a dark or black shade (corresponding to air) surrounding the breast and the breast, which shows a high density (white) skin-line 126, darker (grey) non-glandular, or adipose tissue 124, and the glandular tissue 122 interior to the breast (which appears white).

The volume data set in CT is an accurate depiction of the x-ray properties of the breast throughout the volume of the breast. Each 2D coronal CT image 120 is comprised of individual pixels, each with an area given by the dimensions of the (x, y) pixel (Area=$\delta_x \times \delta_y$). The image also is characterized by a "section thickness," which can be called $\delta z$. These concepts are well known to those skilled in the art of CT. The volume of each volume element ("voxel") is then:

$$V_{voxel} = \delta x \times \delta y \times \delta z.$$

Figure 10:
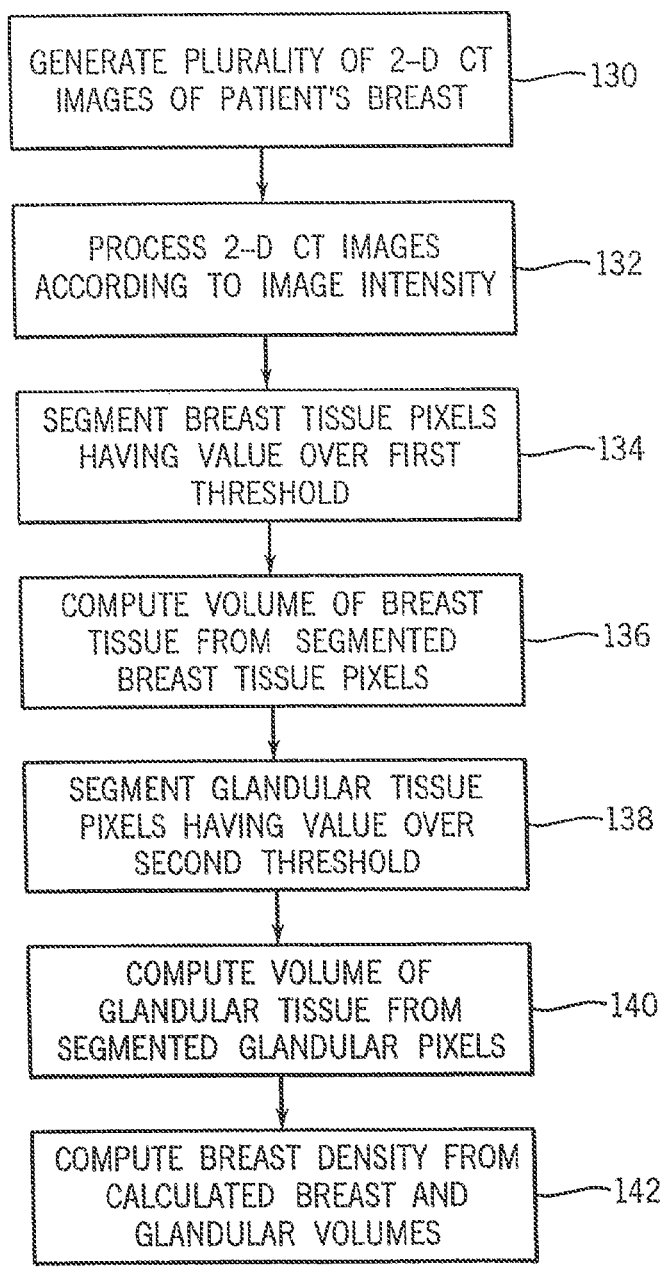
FIG. 10 is a flowchart illustrating a method for computing breast density in accordance with the present invention.
Figure 11:
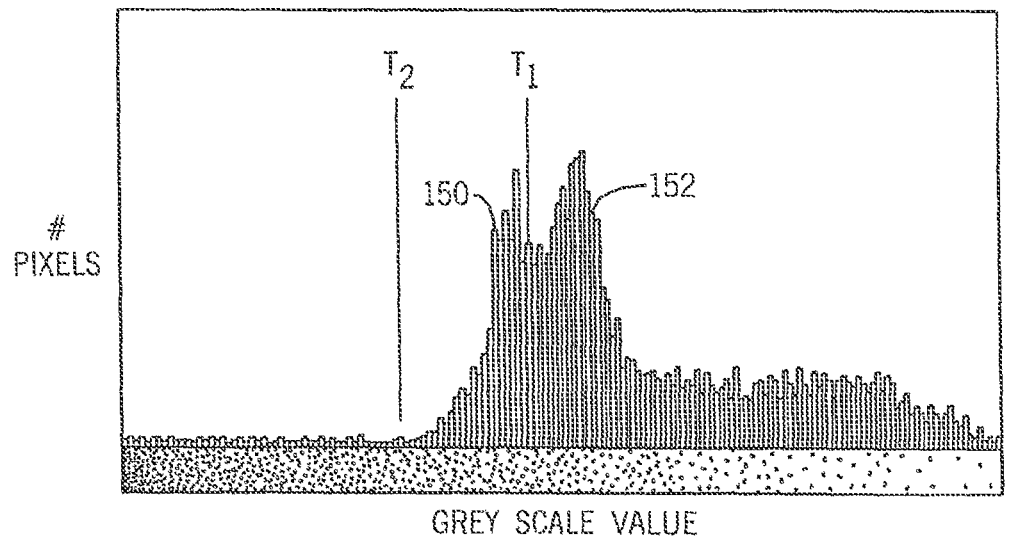
FIG. 11 is a view of a histogram of the image shown in FIG. 10.

In one embodiment of the present invention, the total breast tissue volume can be segmented using the method illustrated in FIG. 10. First, the two-dimensional CT images generated at step 130 are processed according image intensity at step 132. For example, a histogram shown in FIG. 11 may be generated corresponding to the breast CT image of FIG. 9. The ordinate axis represents the number of pixels, and the abscissa represents the grey scale value. The left peak 150 corresponds to adipose tissue 124, and the right peak 152 corresponds to glandular tissue 122. Thus, data points to the left of threshold value T2 are mostly outside of the breast (due to their low image densities), and those voxels of the image that have a gray scale greater than T2 are considered to be inside the boundaries of the breast. The total number of voxels "inside" the breast can be found at step 134 by summing the images from each image over the total number of images in the volume data set. The number of voxels inside the breast $N_{breast}$, can then be multiplied by the voxel volume $V_{voxel}$ to determine the entire breast volume at step 136 with the equation:

$$V_{breast} = N_{breast} \times V_{voxel}$$

To identify the volume of the breast that is comprised of glandular tissue, the same procedure as that outlined in the above paragraph can be used, except that the threshold value T1 is used instead of T2. Voxels having gray scale values above T1 (for example) are not only "inside" the breast, but are also very white voxels as seen in the image 120, and therefore these voxels are those which are predominantly comprised of glandular tissue. The total volume of glandular tissue V gland in the breast is determined by segmenting the pixels above threshold T2 at step 138 to find the number of glandular pixels $N_{gland}$ and then multiplying the number of identified pixels by the voxel volume at step 140 with the equation:

$$V_{gland} = N_{gland} \times V_{voxel}$$

The breast density, β, can then be computed at step 142 as the fraction of the volume of a woman's breast which contains glandular tissue, expressed as:

$$\beta = V_{gland}/V_{breast}$$

Other variations of the above equation may exist and may be useful in characterizing what is known subjectively in the clinical environment as "breast density".

The above breast density calculations may be further manipulated to generate risk assessments in a breast cancer screening regime for individual patients. Since women with higher breast densities are known to have a higher incidence of breast cancer, it is logical that heightened screening procedures (different breast cancer screening tests, more frequent tests, or combinations of different screening tests) would have a higher probability of discovering breast cancer at an earlier stage.

Breast density calculations may be performed on a number of women spanning the age of breast cancer screening, for example from 40 years to 90 years of age. The mean breast density $X_{BD}$ can be determined for a large number of women in each age group (e.g., every 5 years). The mean breast density $X_{BD}$ and the standard deviation in this value $\sigma_{BD}$ can be used to assess the relative breast density of each woman, relative to women in the same age range. Simple statistical tests (such as the student's t test) can then be used to evaluate z-scores, which would establish how well a woman's breast density matches the norms for her age. Women with higher breast density levels would then be considered to have higher risk factors for breast cancer.

Figure 12:
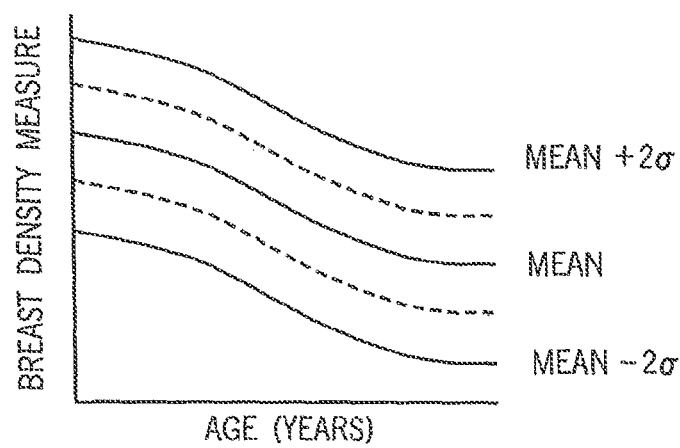
FIG. 12 illustrates breast density as a function of the patient's age.

FIG. 12 shows the hypothetical relationship between breast density and age. These data, which can be generated after enough patients are studied by our breast CT scanner, can then be used to assess the relative (age-adjusted) breast density value for an individual woman.

Histogram-based voxel segmentation can also be replaced or augmented by spatially-based methods for pixel segmentation. For example, standard linear (e.g., convolution or enhancement filters) and non-linear (e.g., non-convolution or morphological filters) image processing techniques commonly used in digital image processing applications may be used at step 132 in combination with histogram methods. Both techniques accomplish their results by examining and processing an image in small regions, called pixel "neighborhoods." A neighborhood is a square region of image pixels, typically 3×3, 5×5 or 7×7 in size.

For example, simple linear smoothing procedures can be used at step 132 to smooth the image prior to histogram analysis Enhancement or convolution filters process image neighborhoods by multiplying the values within a neighborhood by a matrix or "kernel" of filtering coefficients (integer values). The kernel is the same size as the neighborhood that it is being applied to. The results of this multiplication are summed and divided by the sum of the filter kernel. This result then replaces the center pixel in the image neighborhood. For example, a low-pass, gauss or median filter may be used to eliminate detail or random image noise in preparation for segmentation.

Non-linear or non-convolution techniques may also be applied to the image. Unlike convolution filters, they do not multiply the neighborhood values by a kernel of filtering coefficients. Instead, a non-convolution filter works only with the data in the neighborhood itself, and uses either a statistical method or a mathematic formula to modify the pixel upon which it is focused.

An erosion filter is an example of a non-linear enhancement technique that may be used to eliminate the skin boundary from the image. An erosion filter changes the shape of objects in an image by eroding (reducing) the boundaries of bright objects, and enlarging the boundaries of dark ones. The skin boundary, which is not glandular tissue, has gray scale values similar to glandular tissue, and thus can introduce error in determining glandular tissue density. By eroding the skin, only the actual breast tissues would be evaluated in the assessment of breast density, and this process would reduce the confounding nature of the skin voxels in the calculation of breast density. Erosion or other image processing techniques (such as linear Sobel or Roberts edge filters) may be used to essentially redefine the border of the breast tissue volume some finite distance (e.g. $D_{skin}$) from the air-skin boundary.

Thus, Breast CT genuinely enables the calculation of breast density due to the three-dimensional volume data set that is reconstructed with this technology. It is envisioned that the automatic algorithms can be used to produce accurate measures of breast density from the breast CT volume data set, and that these measures could play an important role in the management of individual women.

Although the density and volume measurements are ideal for determining breast density, the methods of the present invention may be used for determining volume and density of a number of anatomical features of the patient.

4. CT image biopsy.

While the breast CT scanner is capable of high-resolution computed tomography scanning, an apparatus of the present invention uses high-resolution techniques to replace physical (needle-core) biopsies. If imaged with sufficient spatial resolution, it is anticipated that the image data itself can serve as an imaged-based biopsy for some women, and this would obviate the need for mechanical insertion of a needle into the woman's breast.

Figure 14:
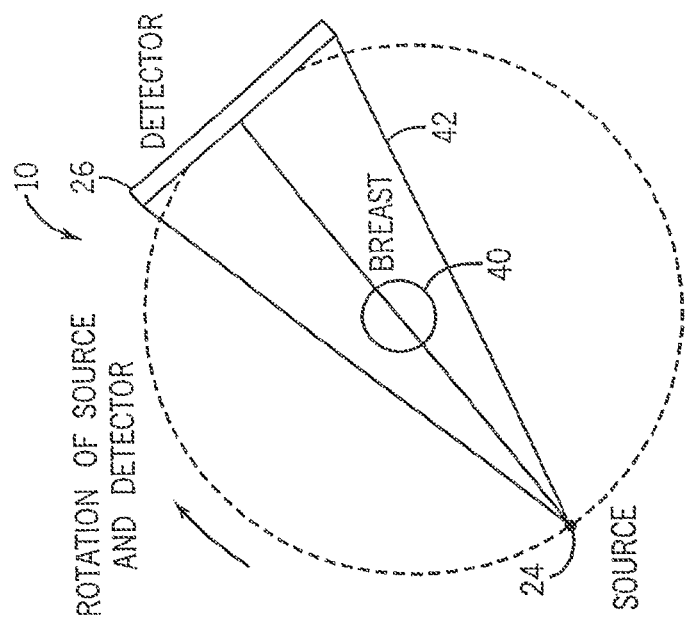
FIG. 14 is a side view of the CT scanner shown in FIG. 13.
Figure 13:
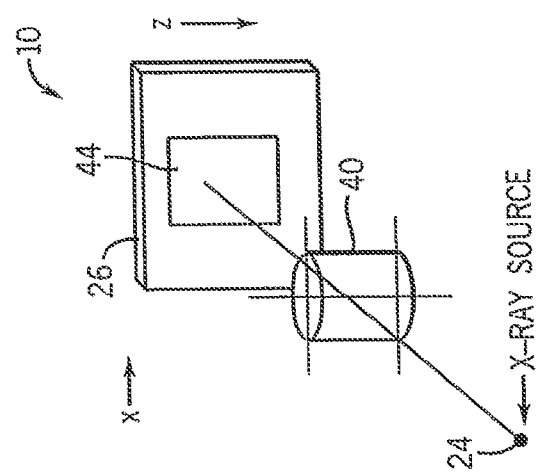
FIG. 13 illustrates a perspective view of the operation of the CT scanner of FIG. 1.

FIGS. 13 and 14 illustrate the typical geometry of a breast CT scanner 10 of FIG. 1, with the breast 40 positioned between the x-ray source 24 and the detector 26. The breast 40 is depicted as a cylinder, and the shadow 44 of the breast is projected onto the x-ray detector 26 as a rectangle in FIG. 13. FIG. 14 illustrates the top-down view of the breast CT scanner 10, with the x-ray source 24 and detector 26 rotating around the stationary breast 40 during the acquisition sequence. Normally, a 360 degree image acquisition is obtained. Generally, detector 26 comprises a 1024×768 matrix (using 2×2 binning) to reconstruct the three-dimensional volume dataset (approximately 300 images, each with 512×512 matrix size). The voxel size of each pixel is approximately 0.20 mm to 0.30 mm. When a suspicious lesion or area in the breast 40 is identified by the diagnostic physician, in mammography (for example), additional views including magnification views are acquired.

Figure 15:
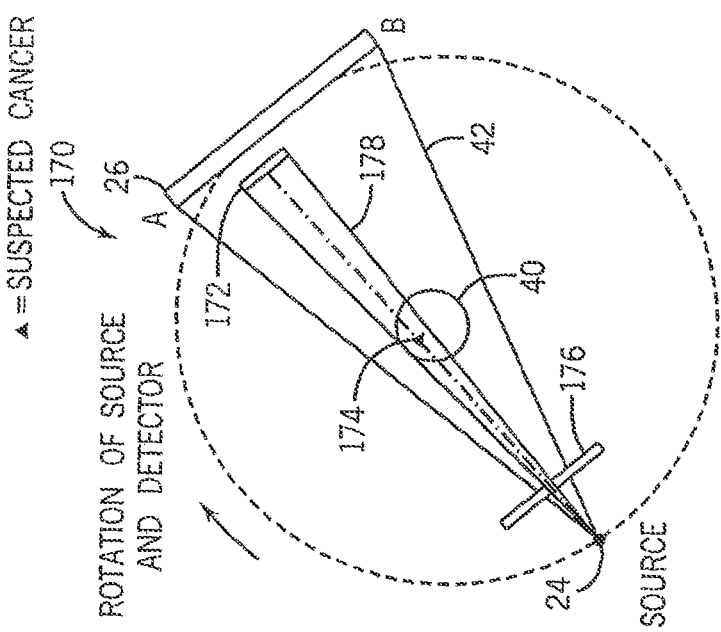
FIG. 15 is a top view of the CT image biopsy system of the present invention

Referring now to FIG. 15, a CT image biopsy system 170 in accordance with the present invention is shown. The CT image biopsy system 170 is configured to generate a high-resolution image of a suspicious region of interest (ROI) 174 in the anatomy of the patient, e.g., a suspected cancer region in the patient's breast 40. By obtaining a focused, very high spatial resolution image where the suspected lesion 174 is thought to occur, a dramatically increased diagnostic potential, approaching that of a needle core biopsy (currently the state-of-the-art for breast cancer definitive diagnosis) may be achieved.

To generate the high-resolution image, a high-resolution detector 172 (e.g., 2048×2048 matrix with 25 µm pixels) is imposed in front (on the x-ray source 24 side) of the breast CT scanner detector 26. For the purposes of this invention, the high spatial resolution detector system 172 for CT image biopsy may comprise a charge couple device (CCD), a ceramic metal oxide semi-conductor (CMOS), a high spatial resolution small field of view thin-film transistor (TFT), or any high resolution x-ray detector system currently used in the art for x-ray acquisition.

Alternatively, the high-resolution detector may be an indirect detector system, where a scintillator, such as Cs1, GD02S2, LaAOBr, Y2T04, etc., is used to convert the incident x-ray beam into light to be subsequently detected by the optical detector system. In another embodiment, a direct detector system may be used, which results in the direct conversion of the x-ray ionization of the detector components into an electronic signal that is amplified and digitized for image formation. Examples of direct detector systems include lead oxide, mercuric oxide, selenium, and other such systems known in the art.

The CT image biopsy system 170 further includes a collimator 176 to focus the wider x-ray beam 42 emitted from source 24 to a narrow field of view 178. By focusing the field of view, the system 170 only interrogates the suspicious region 174 in the breast 40, which is received by the high resolution detector 172. This careful collimation is not only beneficial in reducing the radiation dose to the patient, but also in reducing the amount of x-ray scatter that is imaged.

Figure 16:
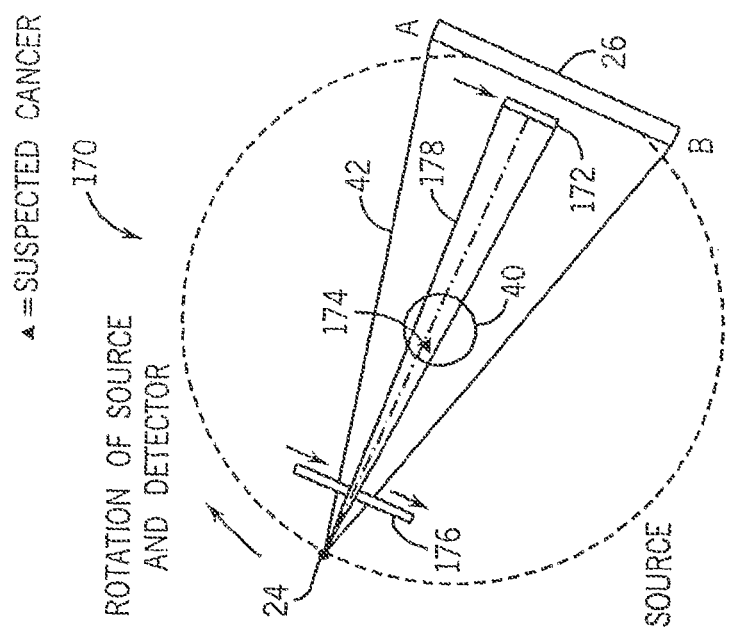
FIG. 16 is a view of the CT image biopsy system of FIG. 15 after partial rotation.

Referring now to FIG. 16, the high-resolution detector 172 and collimator 176 may be configured with additional motion components to adjust the position of the high-resolution detector 172 and collimator 176 during the CT acquisition, depending upon where the identified lesion was in the volume dataset. If the region of interest 174 is exactly at the center of the breast 40, the high-resolution detector 172 and collimator 176 remain stationary with respect to the rotating gantry. However, when the region of interest 174 is located at the periphery of a large breast, the high-resolution detector 172 and collimator 176 move in a sinusoidal fashion as the breast CT gantry rotates around the 360 degrees of motion to intercept the collimated x-ray beam 178.

FIG. 16 illustrates that, during rotation of the CT gantry, the position of both the collimator assembly 176 and the high-resolution detector 172 shift in the X direction (see FIG. 13) in order to remain in the direct x-ray shadow of the region of interest 174. The geometry of the system 170 geometry dictates that the motion of the high resolution detector 172 relative to the low resolution detector 26 (which is fixed to the gantry) will involve a sinusoidal motion, both in the x (lateral) and z (azimuthal) directions for a region of interest 174 that is off-center. The collimators 176 will also follow the sinusoidal motion (e.g., with adjustable collimator jaws), albeit with less amplitude due to the geometrical demagnification. By moving the high-resolution detector system in a sinusoidal motion, the same volume of tissue is imaged over the entire 360-degree scan.

Figure 17:
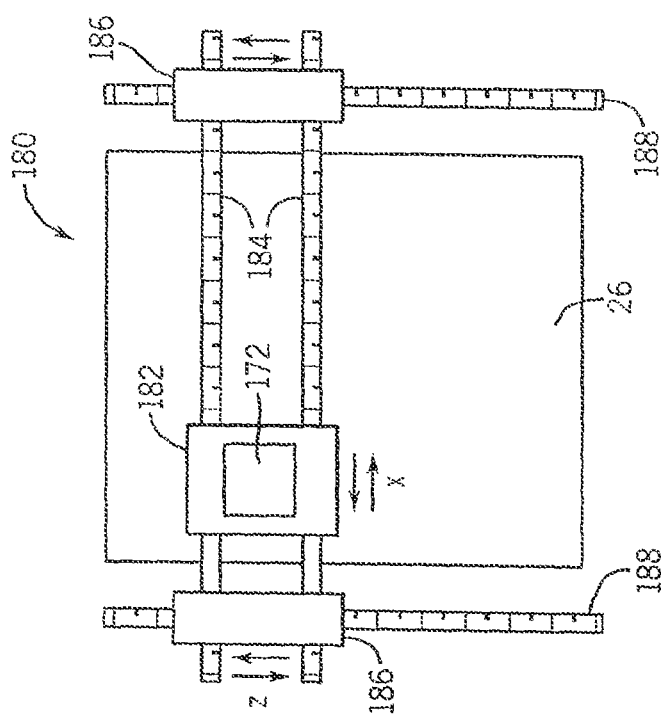
FIG. 17 is a view of the CT image biopsy system of FIG. 15 after additional rotation.

FIG. 17 illustrates yet another view of the high resolution CT image biopsy system 170, having rotated through a larger angle than in FIG. 16. Note that both the collimator assembly 176 and high-resolution detector 172 have moved to keep co-linear with the suspected lesion 174.

Figure 18:
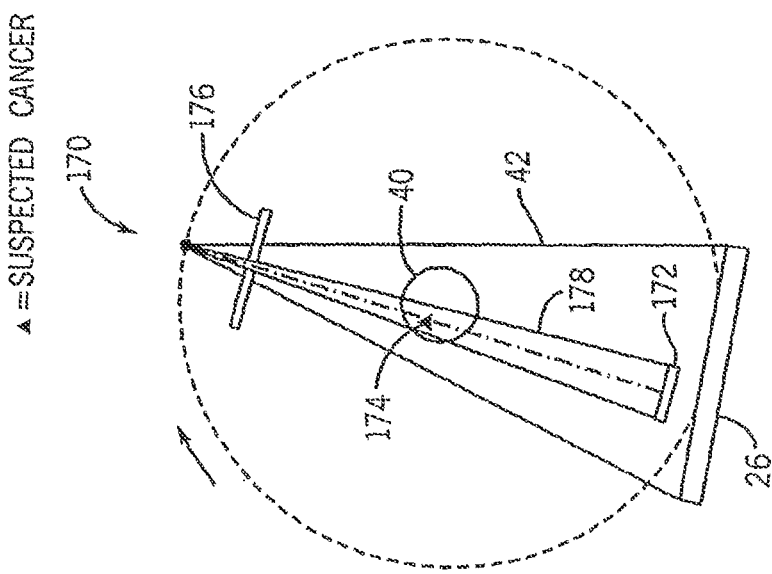
FIG. 18 shows a translational stage for linear actuation of the high-resolution detector of the present invention.

FIG. 18 illustrates an actuation system 180, as viewed from the x-ray source, configured to enable the sinusoidal motion of the high-resolution detector 172. The high-resolution detector 172 has a lead backing 182 to prevent the excess (penumbra) x-ray field from striking the primary breast CT detector 26. To accommodate linear motion in the x-axis (affecting a corresponding sinusoidal motion as the gantry rotates through its range of motion), a worm-drive system may be employed using lead screws 184 and motor-controlled housings 186 to drive the lead screws 184. The lead screws 184 allow the motion of the high-resolution x-ray detector 172 and its backing 182 to move laterally (i.e. the along the x-axis) across the field of view under the computer control. A second set of lead screws 188 may be positioned perpendicular to the horizontally-oriented lead screws 184. The vertically-oriented lead screws 188 are controlled by a second set of motor housings (not shown) to allow the vertical positioning (in the z-axis) of the high-resolution x-ray detector 172.

Alternative embodiments of the CT image biopsy system 170 may include the use of cables (or wires) transported by motor-controlled pulley systems to effect motion of the high-resolution x-ray detector 172 in both the horizontal and vertical directions. Other positioning systems, such as pneumatic positioning systems, systems based upon linear motor technology, or other mechanical devices for translation in one or more axes may also be used.

A further alternative mode of scanning may include the use of a stationary x-ray detector with an x-ray focal spot which moves in a translational matter in both the horizontal and vertical dimensions. Similar means for motivation (e.g. lead screws, linear motors, cable/pulley systems, etc.) can be envisioned for the motion of the x-ray source or collimators 176.

Figure 19:
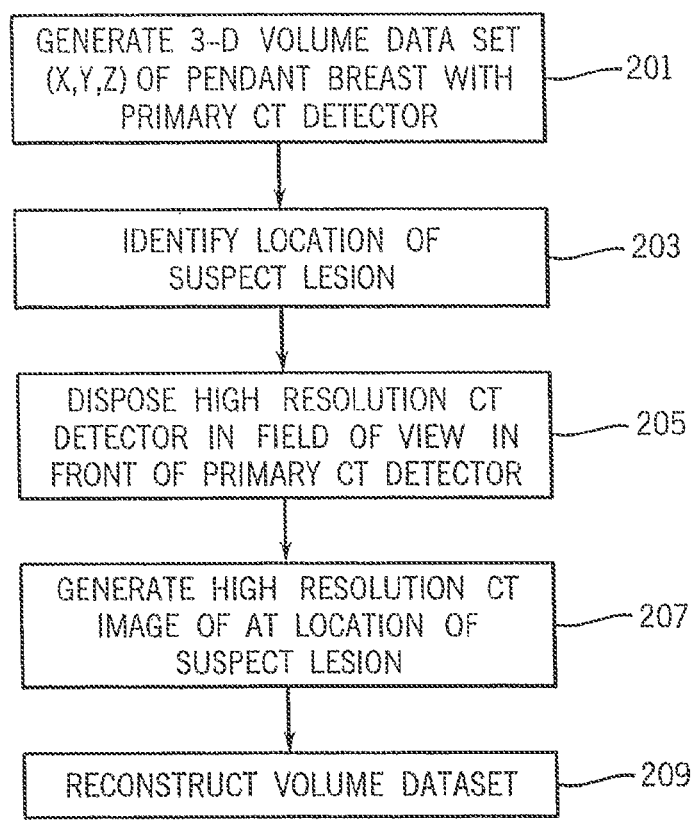
FIG. 19 is a flowchart of a method of performing a simulated biopsy using a CT scanner in accordance with the present invention.

Referring to FIG. 19, a method for performing a simulated, or "virtual," biopsy using a CT scanner is described. First, a scan (step 201 in FIG. 19) of the anatomical region, e.g., the patient's breast, is made using a normal resolution scan on a primary CT detector, (e.g. the 1024×768 detector 26 in FIG. 17). The normal resolution breast CT image data is then used to indicate the specific location that is considered abnormal and in need of further follow up at step 203.

A three-dimensional cursor software, or other algorithm based upon basic geometry, may be used to triangulate upon the coordinate in the breast 40 identified by the radiologist as a region of interest or suspicious lesion breast CT images.

Once a region of interest is located, acquisition of a very high spatial resolution breast CT is performed by imposing a second detector, e.g., the high spatial resolution detector 172, into the field of view of the CT scanner (step 205), and then scanning the region of interest onto the high resolution detector (step 207). During scanning, a computer algorithm may also control the motion of the high-resolution detector and x-ray source, according to the identified location of the region of interest, to maintain focus of the x-ray beam and subsequent detection on the region of interest. After acquisition of the high resolution CT data, further processing is performed (step 209) to reconstruct the image for display.

For breast CT, the spatial resolution of the reconstructed volume dataset depends upon a number of parameters, including the focal spot size, the reconstruction matrix, the mathematical filter, the number of views acquired, and the spatial resolution of the imaging detector. One or more reconstruction algorithms may be employed to condition the moving source geometry relative to the moving detector geometry. The reconstruction algorithm may facilitate placement of the detected high-resolution data in a larger matrix projection image (e.g., from the primary, normal-resolution CT detector), and adapt it for the sinusoid variation of the location of the high-resolution image in terms of its placement into the larger matrix projection image. Generally, only the region corresponding to the high-resolution biopsy zone is reconstructed. To fill in the data set outside of the high-resolution image data (in the larger matrix), projection image data from the low-resolution scan is used. Thus, lower resolution CT scan data for both positioning data and to correct for breast tissue which is outside the field of view of the high-resolution scan. This provides the entire view for the mathematical filtering operation that is used for CT reconstruction.

In general, the high resolution CT image biopsy acquisition sequence may be accompanied by higher exposure rates (increased exposure per frame) and a larger number of acquired views to achieve the higher spatial resolution desired to simulate biopsy of the suspect or target tissue. The reconstruction of the high resolution CT image biopsy volume dataset would also accommodate the position of the detector (or x-ray source if it is being moved), using geometric corrections commonly used in the art.

Figure 20:
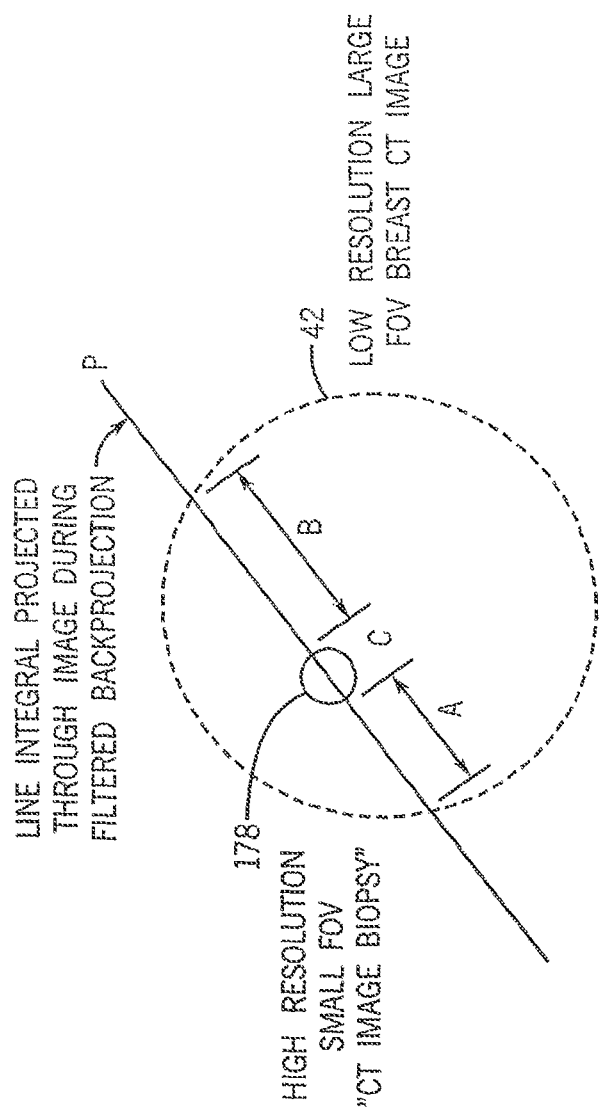
FIG. 20 illustrates a schematic of the field of view of the CT image biopsy system of FIG. 15.

Referring to FIG. 20, additional operations may be performed to correct for artifacts resulting from the high resolution scan. Because the x-ray beam that is focused on the high spatial resolution detector 172 interrogates tissue that is excluded from the cone beam projection image dataset, artifacts may result in the reconstruction of the high-resolution volume dataset. Since the high resolution CT image biopsy is acquired after the acquisition of the normal breast CT image, the additional information needed to correct the high-resolution volume dataset may be supplied by the initial, low-resolution breast CT scan data. The projection integrals associated with the cone beam projection data for the normal (low resolution) CT datasets may then be subtracted from the high resolution CT reconstruction (for the CT image biopsy), to remove the peripheral information which would lead to artifacts. In the context of FIG. 20, a line integral is projected through the image during filtered back-projection. The projection value P is equal to the sum of the components (A+B+C). Thus, to correctly use the projection value C across the field of view of the CT image biopsy, the values of A and B may be determined from the reconstructed low-resolution image, whereas C is computed directly.

Using this type of acquisition, it is anticipated that much higher spatial resolution (perhaps 100 micrometers) may be achievable.

The high-resolution CT image biopsy will provide the additional spatial and contrast resolution (due to the higher spatial resolution of the detector, and the increased radiation levels used to acquire this CT image dataset) to enable diagnosis in regards to breast cancer with increased confidence. The existence of this technology may reduce or eliminate the need for physical forms of biopsy (e.g. incision or needle core biopsy). In addition, it is appreciated that the above methods and apparatus may be used in a number of applications beyond scanning breast lesions. For example, CT image biopsy may be performed on other anatomical regions of interest on the patient wherever traditional biopsy would be performed.

5. Physical Robotic Biopsy.

The CT scanner 10 of FIG. 1 provides exceptional spatial localization capabilities. Consequently, CT image data may be used for performing a high precision and high accuracy biopsy of small tumors using a physician-guided robotic system.

Figure 21:
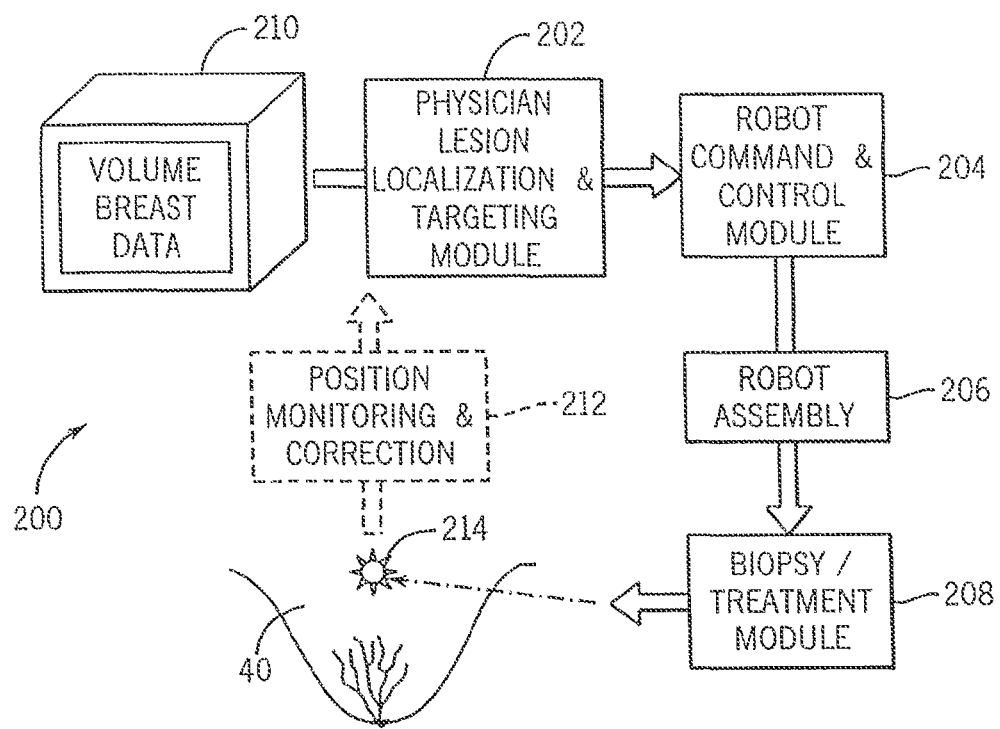
FIG. 21 is a schematic view of an apparatus for performing a CT image data-guided robotic biopsy.

A schematic view of the robotic biopsy system 200 of the present invention is shown in FIG. 21. The robotic biopsy system 200 consists of several modules, including: a volumetric data physician targeting module 202, a command and control module 206, a robotic assembly module 208, and a deployable biopsy/therapy/procedure module. The volume dataset 210 from the CT scanner is input into the targeting module 202 for determination of the lesion location 214. With the target location 214 determined, the control module 204 provides the physician with an interface that intuitively translates lesion coordinates into the desired motion(s) of the robotic assembly 206 for optimization of needle trajectory to the target lesion site. The robotic assembly 206 is small, and sufficiently robust to support a biopsy device that will penetrate the skin and be accurate under load so that positions are rigid and known. The robotic assembly 206 also is radiolucent and yet strong enough to support the range of desired functional operations.

The targeting module 202 and control module 204 are tightly integrated with the scanner hardware and software so imagery is directly available for robotic guidance and localization verification. A position monitoring and correction module may also be incorporated to monitor the motion of the robotic assembly 206 and correct the motion according to input by the physician. After the robotic assembly 206 has been positioned to the proper location, the biopsy/treatment module 208 deploys to administer the biopsy or deliver therapy at the target location within the breast 40.

Figure 22A:
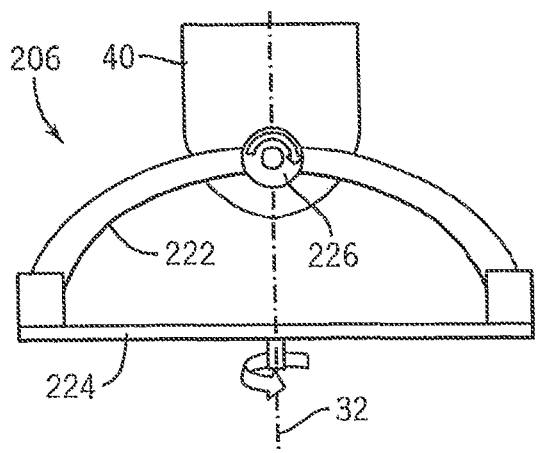
FIGS. 22A and 22B are schematic views of the robotic assembly of the apparatus of FIG. 21.
Figure 22B:
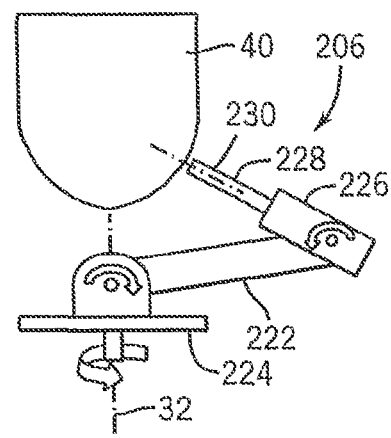

FIGS. 22A and 22B illustrate a preferred embodiment the robotic assembly 206 based on a horseshoe design that pivots upwards and rotates around the scanner's is rotational axis 32 (see FIG. 1) to align the biopsy device with the sampling location 214. The robotic assembly 206 includes a horseshoe-shaped positioning arm 222 that is pivotally mounted to a robotic support platform 224. The robotic support platform 224 is configured to be pivotably mounted to the platform 30 (see FIG. 1) of scanner 10 to facilitate rotation of the robotic assembly about the gantry rotation axis 32. The positioning arm 222 is configured to support manipulator 226, ideally allowing the manipulator to move in four degrees of freedom (DOF), described in more detail with respect to FIG. 24 below. The manipulator 226 is configured to house treatment arm 228, with manipulator 226, at least allowing linear motion of the treatment arm 228 with respect to the manipulator 226. The treatment arm 228 releasably retains treatment instrument 230, such as a biopsy needle, for treatment at the target location. The releasability of the treatment arm's retention of the treatment instrument 230 allows for the treatment instrument 230 to be switched out or cleaned between patients.

FIGS. 23A and 23B illustrate an alternative embodiment of a robotic assembly 240 that incorporates a suspended mount. The robotic assembly 240 has a carriage mount 242 that is configured to mount around opening 16 of CT scanner table 12. The carriage mount 242 is coupled to a horseshoe-shaped positioning arm 246 via gantry drive motor 244. The gantry drive motor 244 facilitates motion of the positioning arm 246 about the gantry rotation axis 32. The positioning arm 246 is further configured to house biopsy manipulator 248 via a manipulator drive motor 250 that allows the manipulator 248 to travel along the track of the hemispherical positioning arm. The biopsy manipulator 248 is shown in a variety of positions in FIG. 23A and at both 0° and close to 90° positions with respect to the carriage mount 242 in FIG. 23B. Cables 252 connect the drive motors to the control module 204. It is appreciated that motion may be facilitated in robotic assemblies 206, 240 by a variety of actuator means, including servo motors, linear actuators, or like devices commonly available in the art.

The breast CT scanner gantry 22 (see FIG. 1) and the robotic assemblies 206, 240 move independently of or in synchrony with each other, making it possible to acquire and use 3D image data to track, correct and perfect needle insertion during procedures.

The breast CT scanner 10 rotates about the breast 40 in an unobstructed cylindrical workspace with an inner diameter of approximately 75 cm. and an outer diameter of approximately 95 cm. The inner diameter of this cylindrical workspace is defined as the distance from the CT source 24 to the CT detector 26. Although this distance is adjustable, its lower bound of 75 cm. was chosen so as to optimize the tradeoff of image resolution and height/cost limitations of the detector.

The height of the cylindrical workspace is defined as the distance from the patient table 12 underside to static platform 30 immediately above the rotating armature 22 supporting the CT source 24 and detector 26. This distance is also adjustable to accommodate breast size variations, but a lower limit of approximately 40 cm. has been found to be optimal. Therefore, the available design space for the proposed robot assembly is a cylinder of 75 cm. diameter and 40 cm height, minus the hemispherical volume occupied by the patient's breast, i.e., the biopsy space.

The CT scanner gantry 22 encompasses the robotic assembly 206, instead of visa versa, for two reasons: first, the more proximal the robotic assembly 206 is to the biopsy space 214, the greater its stability and precision; and second, the robotic assembly 206 materials are selected to minimize x-ray absorption so that the breast 40 can be imaged with the robotic assembly 206 deployed. In this configuration, the robotic assembly 206 partially obstructs the CT projections, so radiolucency makes it possible to obtain views during biopsy device deployment with minimum attenuation artifacts. Partial acquisition reconstruction may also be used to reduce reconstruction artifacts and optimize image quality and robotic feedback and guidance data.

Figure 24:
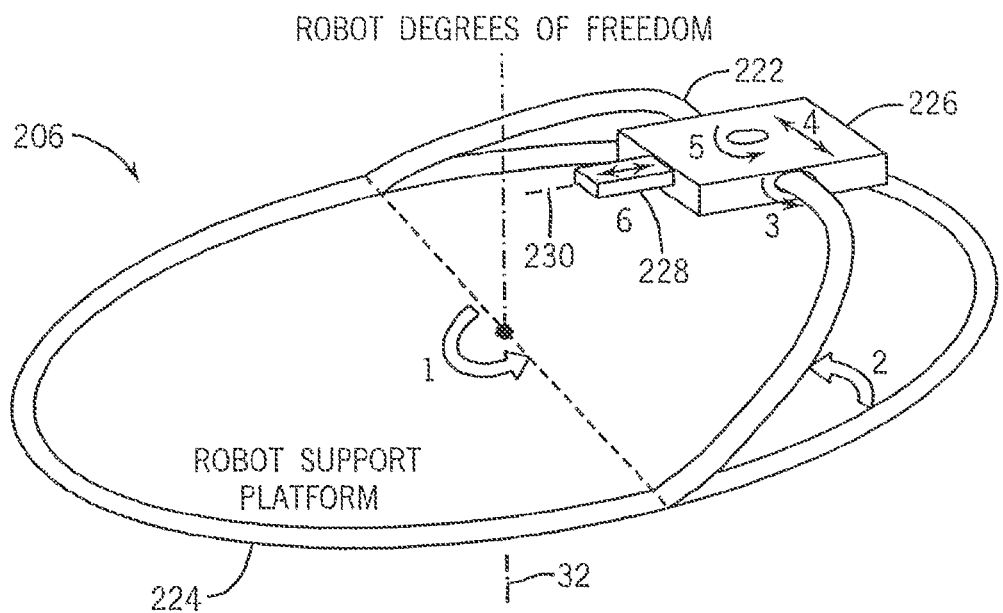
FIG. 24 is a schematic view illustrating the degrees of freedom of the robotic assembly of FIGS. 22A and 22B.

Referring now to FIG. 24, the robotic assembly 206 has one axis of symmetry (the scanner central axis 32) and in the preferred embodiment provides at least five degrees of freedom. The robotic assembly's degrees-of-freedom are as follows: 1) rotation about seamier axis 32 is facilitated by rotation of the robotic support platform 224 about the gantry platform 30; 2) elevation of the support arm 222 upward from the robotic support platform 224; 3) elevational angulation of manipulator 226 with respect to the support arm 222; 4) lateral motion of the manipulator 226 across support arm 222; 5) lateral rotation of the manipulator 226 with respect to the support arm 222; and 6) biopsy needle insertion 230 via linear motion of treatment arm 228 with respect to manipulator 226. It will be appreciated that a number of different combinations of robotic assembly's degrees-of-freedom may be achieved through the separate robotic linkages. For example, the treatment arm 228 may rotationally articulate laterally (and vertically) with respect to the manipulator 226 in addition to, or in replacement of, the same angular articulations of manipulator 226 with respect to the support arm 222.

The robotic assembly 206 provides all needle 230 movements required in a complete breast biopsy exam. The range of desired needle placement motions is as follows:

Primary needle placement is concerned with being able to point precisely to the center point of the biopsy space 214 from any point within the biopsy space. This capability is most critical and has spherical symmetry that is exploited by the robotic assembly's design.

Secondary needle movement provides the ability for a lateral displacement to move laterally away from a given primary needle placement. (e.g. up to +1-10 cm).

Tertiary needle movements are angle orientation changes of the needle from a given secondary needle placement.

Needle trajectory is optimized to minimize lateral forces on biopsy device. Fine adjustment of the needle position and orientation may be made after coarse positioning is completed.

Figure 25:
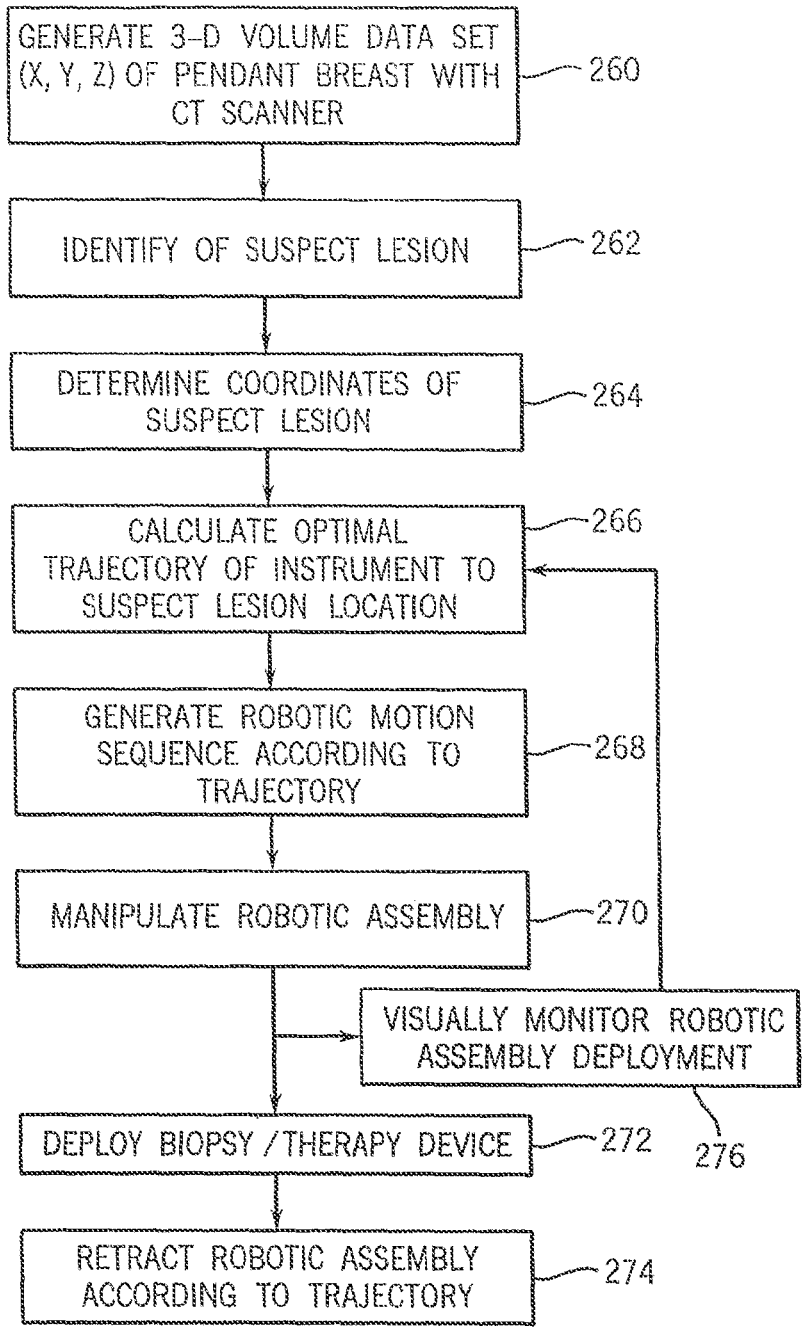
FIG. 25 is a flowchart of the method of performing a CT image data-guided robotic biopsy in accordance with the present invention.

FIG. 25 illustrates a preferred method of the present invention for performing a biopsy (or other treatment) on a patient via a CT image dataset-guided robotic assembly. In a preferred embodiment, the generated volume data set (step 260) is used to localize an area of interest (i.e. lesion, suspicious object, mass, etc.) under physician direction (step 262). Three-dimensional coordinates are determined and corrected to the calibrated reference frame of the object (or patient) at step 264. The multiple view display with co-locating cursor and simultaneous display of actual and synthesized mammogram can be used in identifying the three-dimensional coordinates. For example, using the guidance of the standard mammogram, a cursor can be located in three orthogonal views or on a slice of a multiple slice display to uniquely identify x, y and z coordinates.

An optimized targeting algorithm then determines the trajectory to minimize tissue distortion or damage and avoid intersection with critical structures at step 266. The trajectory algorithm may employ structure avoidance, minimum path, and motion tracking and correction modules to optimize the trajectory.

A control/deployment algorithm then computes the sequence of motions necessary to translate the trajectory into robotic motions at step 268. The control algorithm translates x, y, z coordinates of the lesion derived from the volume data into direction and trajectory instructions for the robot to optimize approach as defined by the physician viewing the original volume data. For example, the control algorithm may employ Jacobian transforms to transform commands from Cartesian space to joint space. Alternatively, the computer can drive the needle all the way to the suspected lesion under image-guided control.

The robotic assembly deploys at step 270 along the path defined to arrive at the optimized position of the platform. Movement of the robotic assembly is therefore precisely controlled. Linear motion is employed for final device or needle deployment to utilize needle rigidity and minimize tissue trauma. Visual feedback (video, ultrasound, and volume images) and deformation of tissues are monitored at step 276 and provided to the operator to monitor deployment, and correct for trajectory in real-time. In particular, an ultrasound imaging probe may provide additional trajectory verification. Analysis software providing compensation for tissue distortion during deployment may also be used. After arrival at the proper position, the operator is notified. The biopsy/therapy device is deployed at step 272 once the operator gives the device the validation command. When the procedure has been completed, the biopsy/therapy device is retracted at step 274 and then the robot assembly is moved to its parked position.

The well-defined geometry of the scanner and the shape of the pendant breast provide several design advantages compared to conventional robotic design: first, the geometry is relatively compact, improving stability of the robot; and second, the azimuthal symmetry of the pendant breast facilitates biopsy access from all orientations around the breast central axis. The design all of all mechanical parts in the robot workspace have minimum displacements of the biopsy needle during positioning and insertion.

The robotic assembly provides a stable platform for breast biopsy that is not distorted due to loading on the robot, either from weight considerations or reactive force to needle insertion. Thus all of the motions of the robot are guided by optimizing needle or device orientation prior to insertion. The net performance of the robot for breast biopsy is a system capable of positioning a needle to within 1 mm. of a defined target.

A physician guided, computer stabilized and image-guided biopsy system provides a more accurate, rapid and less traumatic biopsy of breast tissue, thus producing a very positive impact on early detection and management of breast cancer. Thus, integration of high resolution volumetric breast imaging, image guidance algorithms and medical robotics makes possible more precise biopsy sampling that enhances the physician's ability to locate lesions on the scale of 2-3 mm. in diameter and extract breast tissue samples from those lesions with a consistently high level of precision. Additionally, the increased precision resulting from these techniques also paves the way for other minimally invasive therapy strategies.

The geometric accuracy of the CT machine can be improved by scanning a phantom having radio-opaque markers (small metal beads) aligned along the axis of rotation of the scan offset from that axis. The scan produces a number of projection images over 360 degrees of scanning, and sequential images are analyzed to establish a track showing apparent motion of the markers between images. These tracks can be described mathematically as ellipses and analyzed to reveal characteristics of the geometry of the scanner that are otherwise hard to measure (e.g., the exact location of the focal spot of the x-ray tube within the tube envelope). Knowledge of the geometrical aspects of the scanner allows better determination of actual coordinates from image data. Geometric distortions are also accommodated to some degree by the ability to image the robotic biopsy systems with the same scanner before and during the biopsy procedure. Any geometric distortion applies to both images, thus decreasing its effect on biopsy needle placement.

6. CT Breast Scanner with PET.

One advancement in locating malignant tumors in the body has been the development of PET (Positron Emission Tomography) scanners. PET is a nuclear medicine technology that uses radioisotopes to allow the noninvasive diagnostic imaging of metabolic processes in various organ systems of the human body. Images are obtained from positron-emitting radioactive tracer substances (radiopharmaceuticals) that are usually administered intravenously to the patient. Whereas computed tomography (CT) and magnetic resonance imaging (MRI) provide information about anatomic structure, PET can image and quantify biochemical and/or physiological function. This information is potentially valuable because functional changes caused by disease are frequently detectable before any structural abnormalities become evident.

One embodiment of the present invention comprises a positron emission tomography (PET) detector mounted onto the gantry arm 22 of the breast CT scanner 10 shown in FIG. 1, such that simultaneous acquisition of PET images with the breast CT images can be accomplished. The PET image data will provide information with regards to the functional status or physiology of areas in the breast, including glucose metabolism and other functional or physiologic parameters. The CT scan will require a shorter period of time for acquisition, so the simultaneous image acquisition refers to the dual modality imaging without repositioning the patient. The positron emission tomography image data can be overlaid onto the anatomical images provided by the breast CT, thereby providing the radiologist or other physician with an excellent map of the functional characteristics of breast tissues. In addition, the CT data may be used to provide attenuation correction for the PET data.

7. Breast Restraint and Immobilization.

Referring now to FIGS. 26-30, a method and apparatus are disclosed for the stabilization of compliant, or deformable, structures so that they may be evaluated and manipulated in a controlled fashion. While the specific application of the invention is the stabilization of breast tissue for applications, such as breast imaging, biopsy and other procedures, the broader applications of this invention extend to other biological tissues and areas beyond the medical arena.

Figure 26:
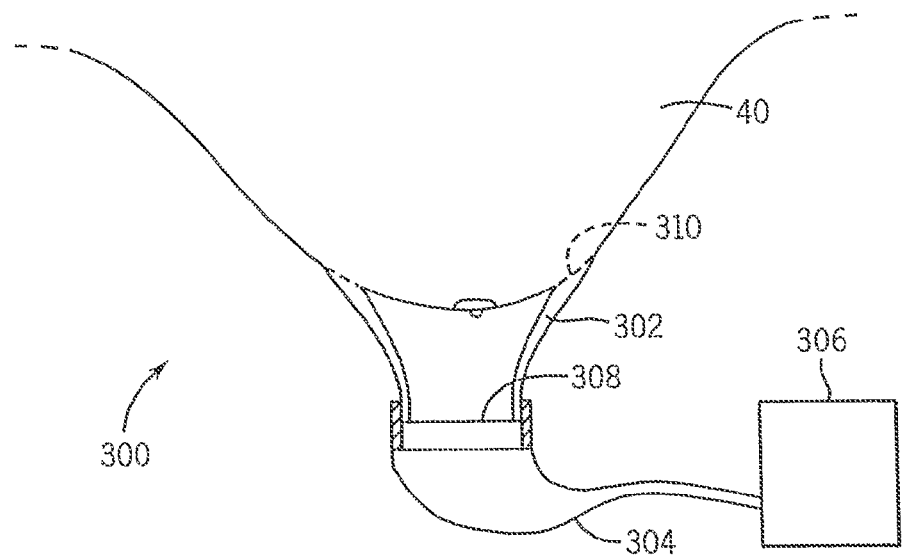
FIG. 26 is a schematic view of a breast restraint device in accordance with the present invention.

In a preferred embodiment illustrated in FIG. 26, a breast immobilization device 300 comprises a vacuum appliance 302, or suction cup, made of a compliant material, such as silicone, and sized to contact a small region of tissue of breast 40. The vacuum appliance 302 is coupled to a vacuum source 306 via a tube 304. The vacuum source 306 is configured to apply a contact vacuum on the interface surface 310 of the vacuum appliance 302, such that a slight tensile force may be applied to the breast 40 to restrain the breast from motion. After placement of the appliance 302 in contact with the skin surface, a vacuum is applied to the appliance 302 that then immobilizes the skin surface and extends to deeper tissues. For example, the appliance 302 may be used to stabilize a region of the breast 40 with a suspicious lesion at a depth below the surface.

Figure 27:
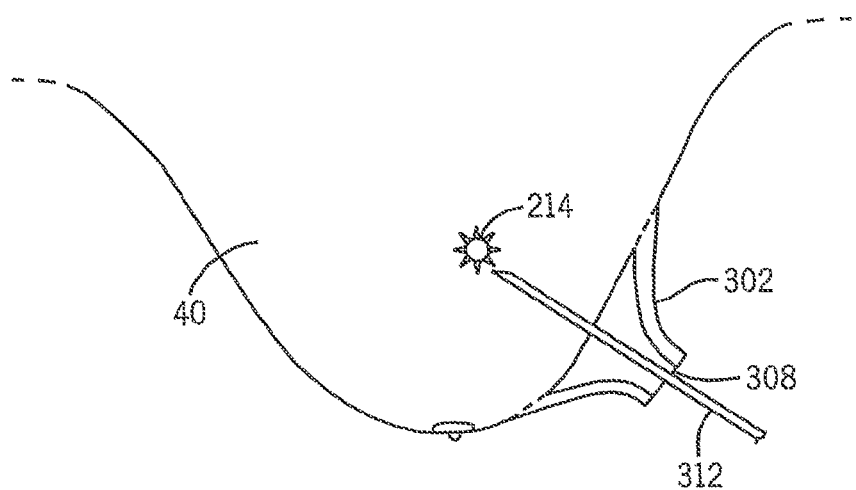
FIG. 27 is a schematic view of a breast restraint device of FIG. 26 used in combination with a biopsy needle.

Referring to FIG. 27, an interventional device 312 (e.g. biopsy needle, miniature surgical instrument, etc.) may be deployed through an access port 308 in the vacuum appliance 302 and extended through superficial tissues to a target lesion 214 where the appropriate procedure is performed. Through the multiplicity of orifices, a sufficiently large area of tissue may be stabilized to permit high-resolution imaging or other procedures to occur without localized tissue motion.

Figure 30:
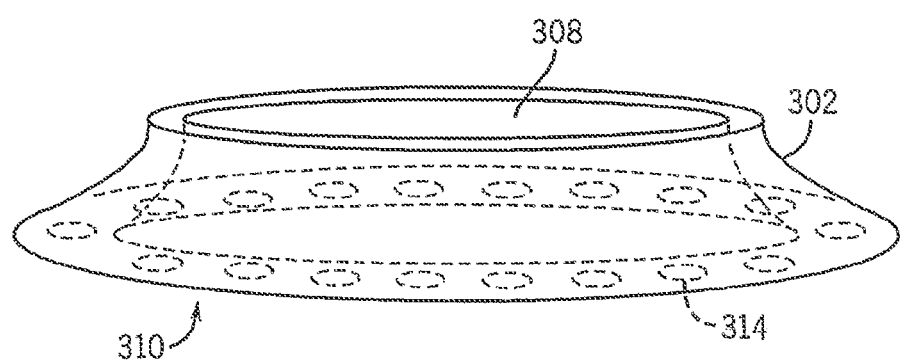
FIGS. 28-30 illustrate alternative geometric configurations of the suction cup of the restraint device of FIG. 26.
Figure 29:
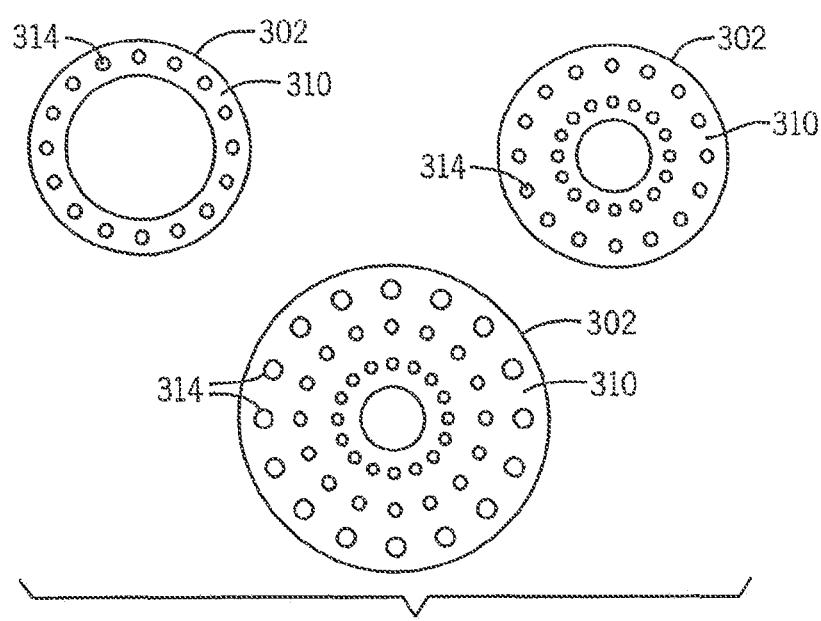

Referring to FIGS. 28 through 30, the interface surface 310 may have a plurality of small orifices 314 in communication with the suction tube 304, such that the suction may be applied evenly across the interface surface 310.

FIG. 29 illustrates a vacuum appliance 302 having a larger interface surface 310 for retention of the tissue. The orifices 314 may be circular, elliptical, rectangular etc., and typically will measure 0.1 mm. to 5 mm. in diameter.

The geometry and construction of the vacuum appliance 302 are such that it can be readily sterilized for surgical procedures. Further, the vacuum appliance 302 is of sufficiently simple design that production costs will be minimized, permitting mass production and disposable usage.

The immobilization device 300 may be used for retaining the breast during scanning, minimally invasive device placement, or even for invasive procedures. Breast immobilization would be highly beneficial for high-resolution breast imaging, and for longer procedures, such as PETICT or radiation therapy. During physical biopsy, the immobilization device 300 prevents the breast from recoiling under the force of an applied needle puncture.

8. Radiation Therapy.

Once a breast tumor is located on the breast CT volume data set, the imaging system of FIG. 1 may be used in a high x-ray output mode to actually apply radiation therapy to the site of the lesion.

While high energy radiation beams produced at 2 MVp and higher are the typical photon beams used in radiation therapy associated with both body and breast tumors, due to the smaller dimensions of the breast and the low density composition of the breast (typically), it is possible to achieve highly concentrated radiation profiles in the breast using lower energy (kVp- or less than 1 MVp) radiation beams. Furthermore, the unique and nearly symmetrically cylindrical profile of the female breast when interrogated by a pendant geometry breast CT scanner, lends itself ideally to the use of relatively low energy x-ray spectra (e.g. heavily filtered 160 kVp, 320 kVp, up to 640 kVp).

In a preferred embodiment of the present invention, a method is disclosed for using a breast CT scanner for energizing the x-ray system at higher x-ray energies (e.g. 80 kVp or 100 kVp) for breast cancer diagnosis or diagnostic examination and using a 160 or 320 kVp (etc.) x-ray beam for radiation therapy treatment. The advantages of a breast CT scanner in regards to the application of radiation therapy is the increased spatial resolution accuracy that can be achieved on a per-fractionation basis with this modality. With each x-ray fraction, a complete diagnostic breast CT scan (employing a cone beam, fan beam, or a hybrid fan beam/cone beam system) can be acquired with the patient lying stationary on the CT table. The treatment volume (typically constituting both the tumor and an appropriate margin) is highlighted by the radiation oncology professional after the breast CT volume dataset is reconstructed, using three-dimensional software and 3-dimensional image cursor technology commonly available to one skilled in the art. Once the treatment volume has been identified by the radiation oncology professional, the breast CT scanner x-ray system can be energized at higher x-ray energies and at higher mA levels (e.g. 320 kVp and 20 mA) and a radiation therapy application can be applied to the identified target volume using rotational therapy techniques also available in the art.

Figure 32:
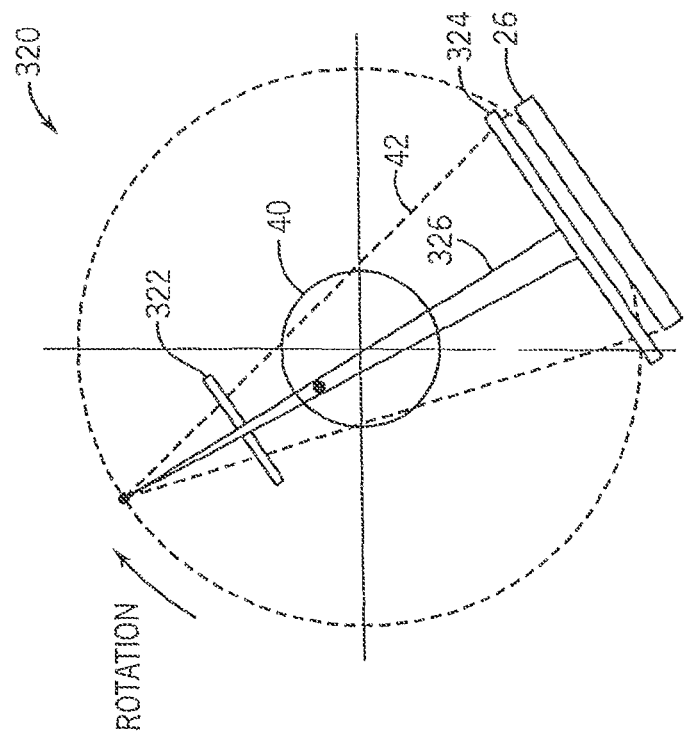
FIG. 32 shows the device of FIG. 31 through partial rotation.
Figure 31:
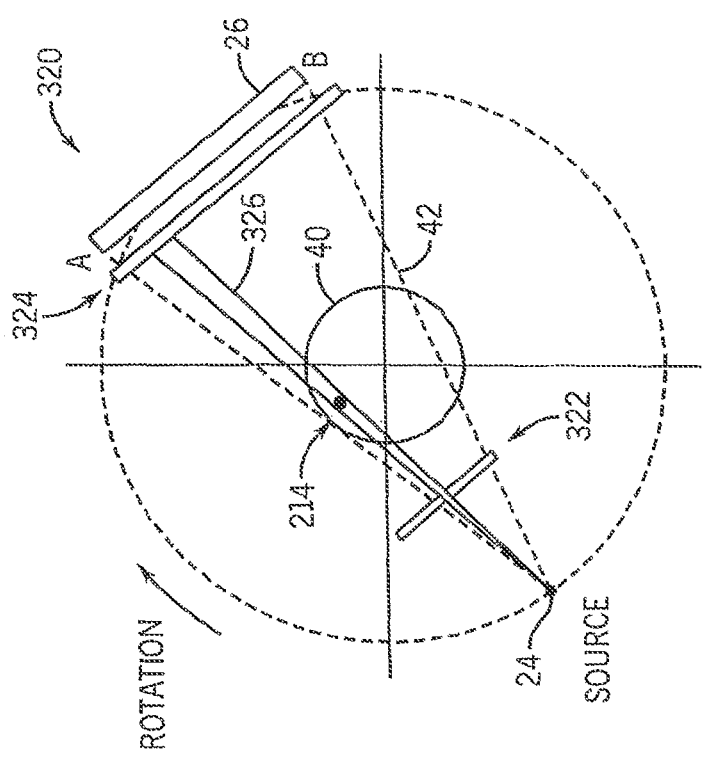
FIG. 31 illustrates a CT based radiation therapy assembly in accordance with the present invention.

In order for the x-ray beam to be collimated exclusively on the target volume as the x-ray source rotates 360 degrees around the breast hanging in pendant geometry, a CT radiation therapy system 320 with translating collimator system 322 (both in the x and z, or horizontal and vertical directions) is shown in FIGS. 31 and 32. FIG. 31 shows the top-down view of the breast CT scanner, including the x-ray source 24, x-ray collimator system 322, and detector 26 for breast CT acquisition. The breast 40 is illustrated as a circle in the center of the scan region (typically referred to as the isocenter). After the diagnostic breast CT acquisition, reconstruction, and interpretation, a cancer volume 214 can be identified by the treatment physician as indicated by the black circle. This treatment volume may be exactly at the isocenter (not shown), or it could be at some distance away from the isocenter (as shown in FIGS. 31 and 32).

To enable the higher energy x-ray radiation therapy of this lesion away from the isocenter, a preferred embodiment includes the translation of a radiation shield 324 in front of the x-ray detector 26 to protect it from the high radiation levels associated with radiation therapy, but also to attenuate the radiation beam so as to record it and reconstruct the treatment volume, which can subsequently be overlaid onto the diagnostic breast CT volume dataset. Software for overlaying the reconstructed treatment volume with the diagnostic breast CT image may also be incorporated.

As the breast CT radiation therapy system 320 rotates around the breast, as depicted in FIG. 32, the collimator assembly 322 translates accordingly (in a sinusoidal fashion as described above for CT image biopsy and associated FIGS. 13-20) such that the high energy/high intensity x-ray beam 326 interrogates the designated treatment volume 214.

Figure 33:
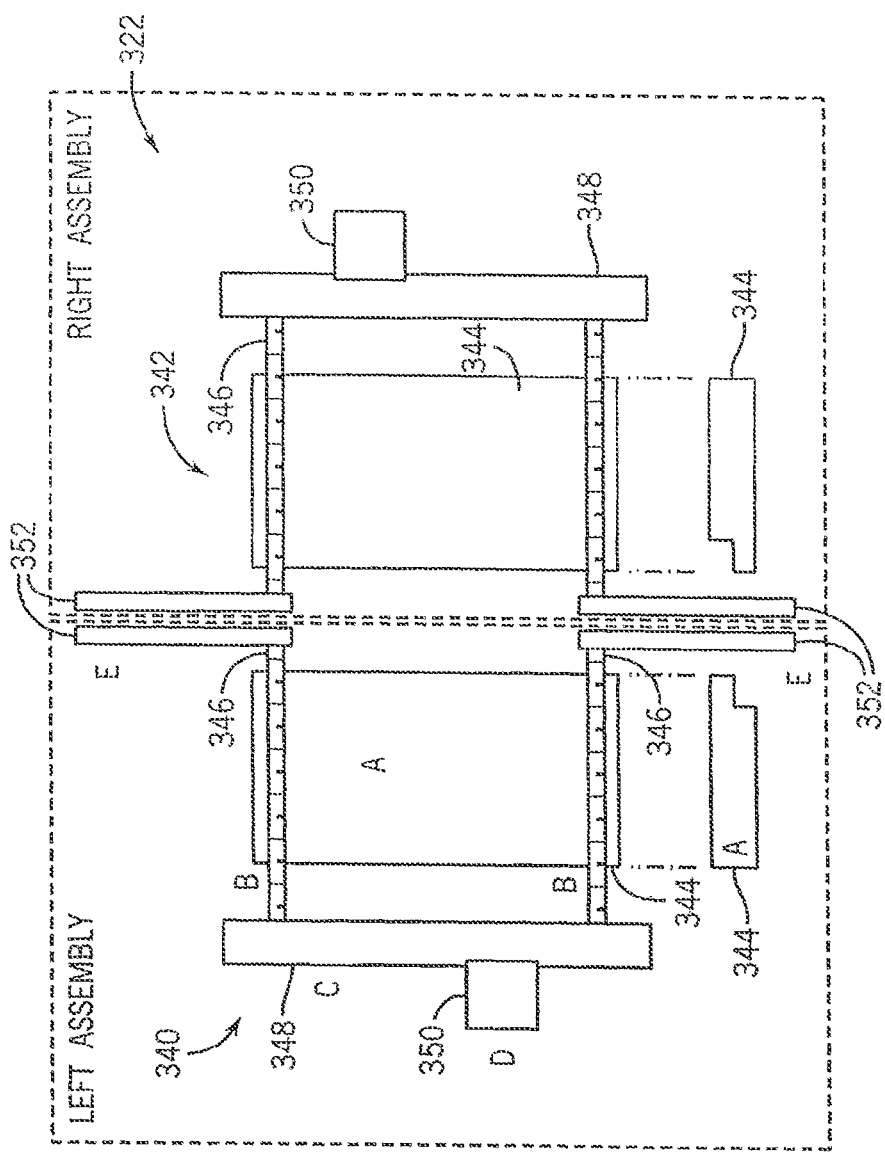
FIG. 33 is a horizontal collimator assembly of the device of FIG. 31.

FIG. 33 illustrates the collimator assembly 322 in a basic format to target the radiation therapy. A left collimator assembly 340 has the components as follows: a thick lead (or other highly attenuating material) x-ray shield 344, lead screws 346 or other translational mechanical devices, a stationary mechanical framework 348, which houses a computer-controlled motor 350 (e.g., stepping or servo motor) that rotates lead screws 346, resulting in the horizontal translation of the x-ray collimator shield 344. A mechanical end-piece 352 is provided to allow stabilization of the other end of the lead screws 346 near the center of the beam. The right collimator assembly 342 is essentially the mirror image of the left collimator assembly 34 with working components as identified previously.

Figure 34:
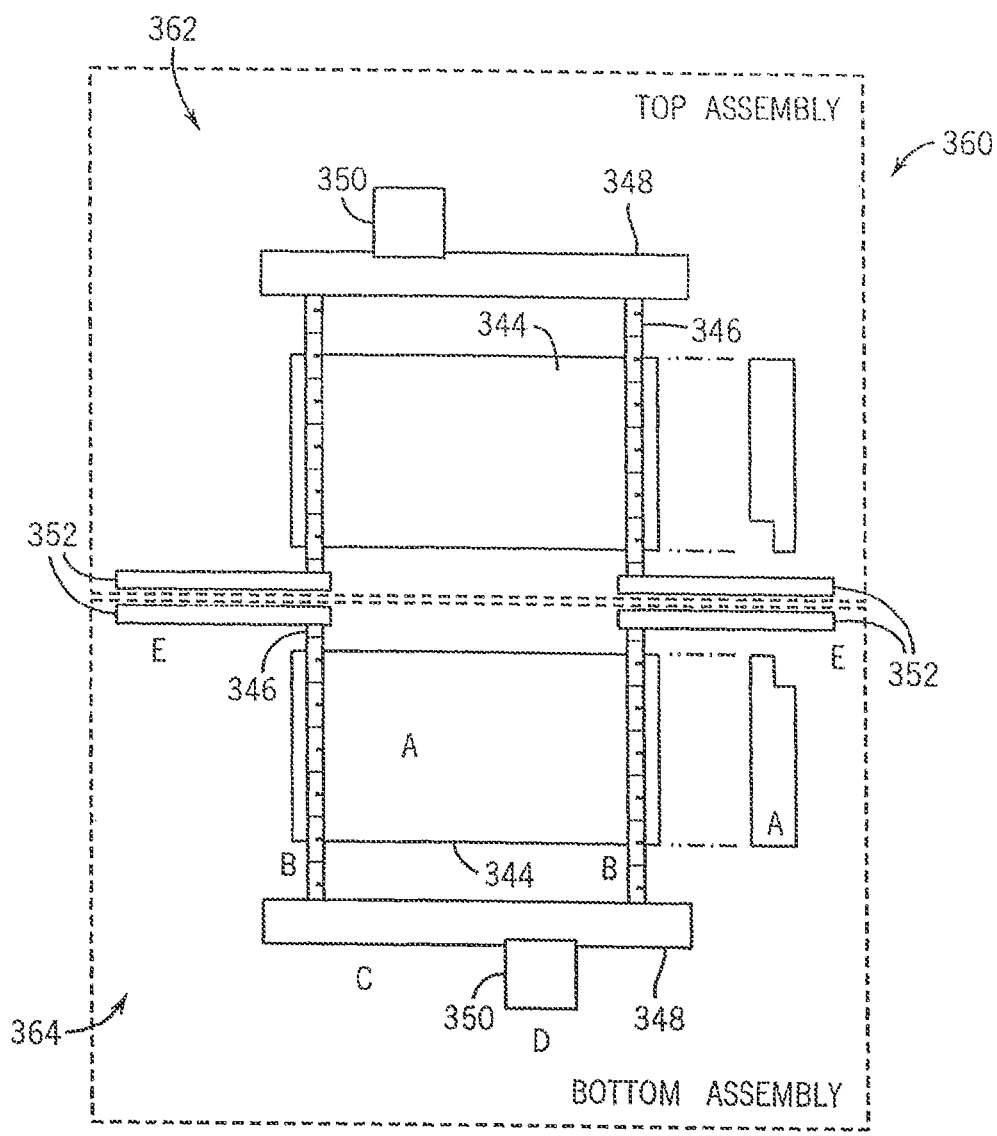
FIG. 34 is a vertical collimator assembly of the device of FIG. 31.

FIG. 34 illustrates a vertical collimator system 360 used for the breast CT radiation therapy system 320. This system allows the independent vertical translation of colliniator blades using both a top assembly 362 and a bottom assembly 364, as depicted. The vertical collimator system 360 incorporates the same components as the horizontal collimator of FIG. 33 (x-ray shield 344, lead screws 346, stationary mechanical framework 348, motor 350, and mechanical end-piece 352) adjusted 90 degrees.

The translating collimator assemblies 322, 362 are translated horizontally and vertically using a cable/pulley system (not shown) or other mechanical translation technology, which can be enabled under computer control, instead of the lead screws as shown in FIGS. 33-34. The drive mechanisms for these mechanical translation systems may include stepping motors, linear motors, servo motors, and direct rotary motor systems known in the art.

Figure 35:
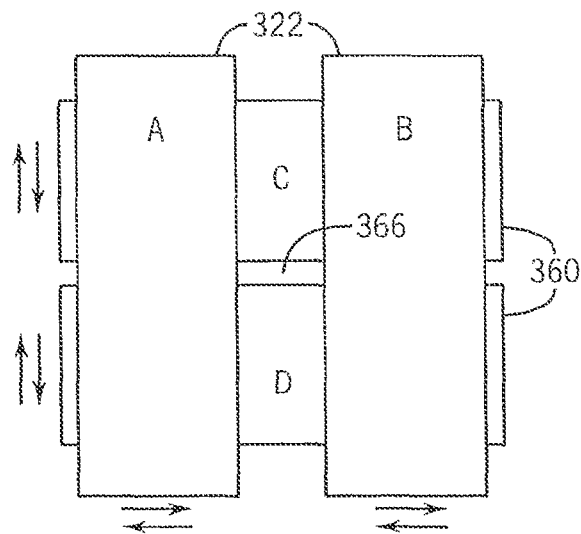
FIG. 35 is a schematic view viewed from the x-ray source of the collimator assemblies of the device of FIG. 31.
Figure 36:
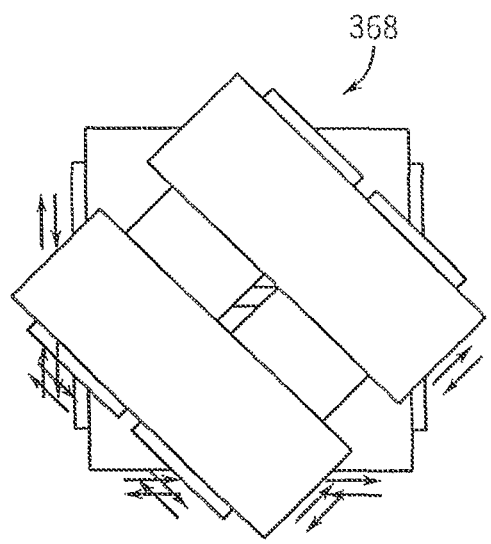
FIG. 36 illustrates the view of FIG. 35 with an alternative 8-panel collimator assembly.
Figure 37:
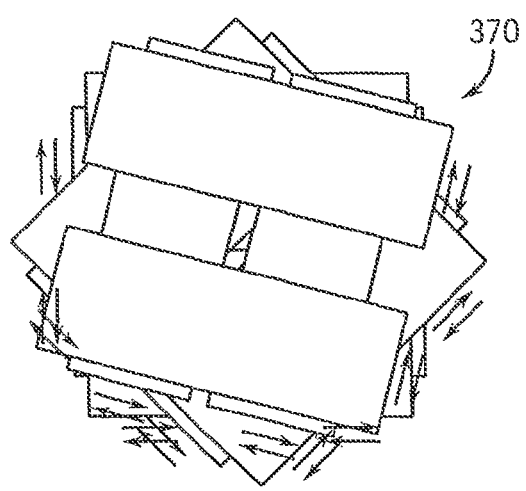
FIG. 37 illustrates the view of FIG. 35 with an alternative 16-panel collimator assembly.

FIG. 35 illustrates the view from the x-ray source with both the horizontal collimator system 322 and vertical collimator system 360 in the field of view, resulting in a rectangular x-ray beam 366 profile. Multiple collimator assemblies, such as the 8-blade collimator system 368 of FIG. 36, 16-blade collimator system 370, or even a 32-blade system (not shown) may be used to further define the x-ray beam profile better circumscribe circular lesions 214 identified within the breast 40. Furthermore, collimator blades, which have circular, linear, or finger-like projections relative to the treatment volume, may be used to enable more complicated and more exotic treatment volume profiles.

The benefits of the relatively low-energy radiation therapy treatment system described herein, compared to MVp photon beams, include the higher spatial resolution that the system affords, both by having per-fraction target volume identification, and a smaller focal spot (which yields higher spatial resolution both for imaging and radiation therapy treatment), and consequently a sharper profile x-ray beam due to the lower energy (less oblique collimator penetration) and the smaller focal spot (smaller penumbra) typical of kVp x-ray imaging systems.

Additional components of the CT radiation therapy system 320 described above include a software module to enable a per-fraction basis, models for acquisition of a diagnostic breast CT exam data and the subsequent reconstruction of a volume dataset, a computer-aided or human-guided (or combinations of above) identification of a 3-D tumor margin and treatment volume module, and computer software necessary for driving the multiple collimator assemblies to deliver the targeted radiation therapy beam to the treatment volume.

A software module may also be included to modulate the kVp-x-ray energy, depending upon the position of the treatment volume relative to the isocenter and breast volume during the scan. For example, the kVp would be increased when the amount of tissue that needs to be penetrated between the entrance beam and the tumor location increases, and a reduction in kVp as the distance between the entrance site and the tumor volume decreases. Software algorithms may further be used to determine the optimum x-ray energy to optimize the radiation deposition of a tumor in a breast at a given thickness, which in turn enables the modulation of the kVp during rotational radiation therapy using the breast CT scanner and radiation therapy systems.

Other investigators have described the use of the injection of high atomic numbers (Z) materials, which preferentially leak into and consequently surround the breast tumor in breast cancers to induce a shower of high linear energy transfer (LET) particles near the site of the tumor. Examples of these high Z agents include an iodinated contrast agent for CT or x-ray imaging, or gadolinium-based contrast agents for MRI imaging. Other high Z agents are envisioned.

While these concepts have been previously disclosed by other investigators, one embodiment of the current invention is a method of scanning a region of interest with a radiation therapy breast CT along with the use of injected contrast agents to achieve increased therapeutic ratios for the treatment of breast cancer. An increased therapeutic ratio is achieved in this embodiment because the low energy (kVp) radiations are preferentially absorbed by the presence of the contrast agent (using k-edge absorption techniques, well known- to those skilled in the art). Once the atoms associated with the contrast agent absorb the radiation beam, subsequent radiations are emitted locally to the site of those atoms, which are situated in close proximity to the breast cancer tumor. The subsequent re-emission of lower energy x-rays and electrons has the effect of concentrating the therapeutic effect of the radiation at or near the site of the tumor for a more lethal effect than the incident beam itself.

Examples of the secondary radiations include K, L, and M fluorescent radiations (x-ray photons), as well as Auger electrons and other cascade electrons associated with x-ray absorption. The net effect of this embodiment is to selectively deliver higher radiation dose levels at the site of the tumor, both by the selective nature of contrast agent secretion near the site of the tumor, and the selective spatial irradiation achieved by the breast CT radiation therapy apparatus. Thus, combining radiation therapy at kVp x-ray energies with the injection of contrast injections may therefore lead to therapeutic ratios similar to, or better than, conventional radiotherapy techniques.

Figure 38:
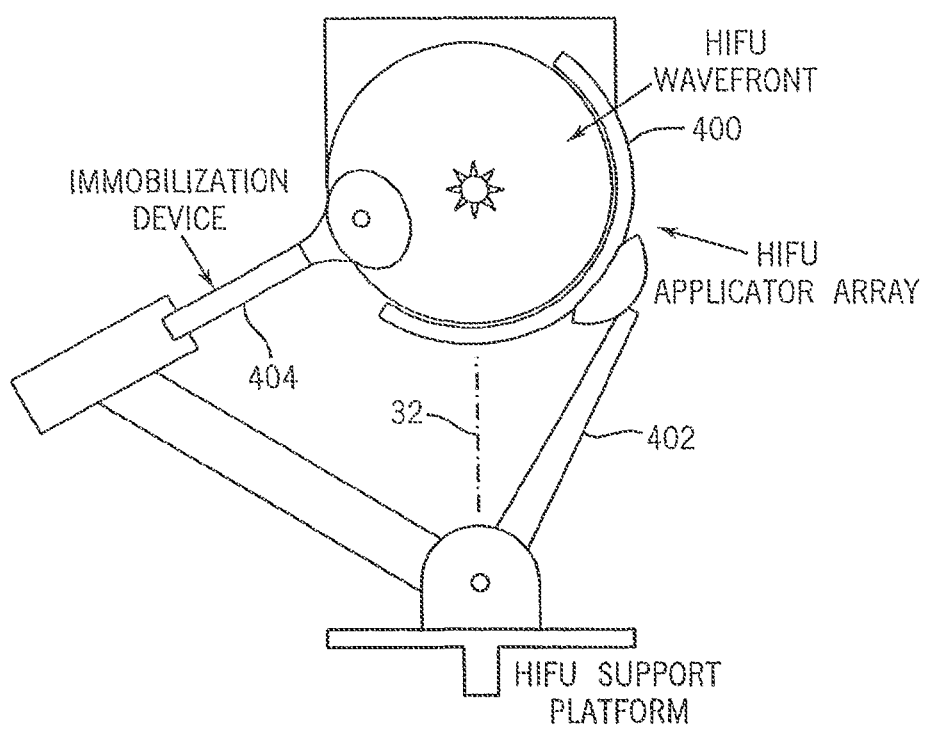
FIG. 38 illustrates an ultrasound based therapy assembly in accordance with the present invention.

Referring now to FIG. 38, as an alternative to radiation therapy, high intensity focused ultrasound (HIFU) may be used for treating small lesions in the breast, making use of the precise location of the coordinates of a tumor determined as described above. In such a system, an HIFU application array 400 may be positioned against the skin of the breast coupled with a suitable acoustic coupling material and as held by a robotically controlled arm 402 similar to any of the mechanical biopsy placement systems described above. The application array 400 may be constructed to provide a properly phased wavefront that passes into the breast to converge on the site of the lesion to provide ablating energy to kill any cancer cells at a focal point. The phasing may be provided by well known phased-array techniques or by proper shaping of the array 40. The array 400 may work in conjunction with the immobilization device described above or a separate immobilization arm 404 may be used. Again, real time imaging can be used to ensure proper registration of the focal point of the array 400 and the lesion.

9. Breast CT Dosimetry.

One embodiment of the present invention comprises a method for measuring the standard dose that is achieved during conventional two-view mammography. The techniques used for producing the breast CT images disclosed in Boone et al., Dedicated Breast CT: Radiation Dose and Image Quality Evaluation, previously incorporated by reference, may be used to determine the dosage for two-view mammography. These results may then be used to tailor the radiation dose from breast CT to be substantially similar or identical to that of two-view mammography.

10. Dual Energy Projection Mammography.

The breast CT scanner consists of an x-ray tube, opposed to an x-ray detector, mounted on a rotating gantry system. If iodine, gadolinium, or some other contrast agent is injected into the breast, dual energy images can be acquired using this same x-ray detector system without rotating the gantry. Instead of acquiring tomographic data, this procedure would allow the acquisition of projection image data sets. By using one low-energy acquisition, and one high-energy acquisition, with suitable processing, a dual energy subtraction image can be produced which highlights the tumor and makes it more visible from the background breast tissues. Monitoring the time-change in tumor contrast (following the wash-in and wash-out kinetics) is also disclosed as a possible diagnostic tool.

11. Calibration Phantoms

In a breast CT, it is important for reconstruction algorithms used to reconstruct the acquired image data to make use of the geometry in which the images were acquired. To enable this, a method of the present invention uses a phantom consisting of a series of BBs placed in the field of view to be imaged by the breast CT scanner. The individual BBs are then tracked using a tracking algorithm, and then the paths of each BB are used to computer-fit the geometry of the scanner. This technique is a highly beneficial component of producing high-resolution CT images without artifacts.

In addition to geometrical phantoms, phantoms comprised of various breast-like materials may be used to enable the accurate calibration of the CT image numbers (typically called Housefield units, HU). Accurate computation of the HUs in the breast CT will enable better differentiation between adipose tissues, glandular tissues, microcalcifications, and breast cancer.

12. Three-Dimensional Breast CT Display.

As described above with respect to FIG. 6, one embodiment of the present invention comprises display techniques for optimally demonstrating the three-dimensional anatomy of the breast for diagnosis. Specifically, a three-orthogonal view display package is disclosed, which enables the evaluation of the breast CT data from any arbitrary reference point. An embodiment comprises simultaneous display of the axial, coronal, and sagittal images of the breast. In addition, other custom rotations controllable from input from a computer mouse may be achieved. Furthermore, alignment lines may be used on the computer monitor to allow a specific location within the breast to be identified simultaneously on all three (or more) images of the breast. The display software for rendering the CT volume data set may also include the generation of mammogram-like images, so that the radiologist can compare the tomographic images with an image that is more similar to their training. The computer-generated mammographic images can also be accompanied by the actual digital mammographic images for that woman.

13. Computer-Aided Detection Computer-Aided Diagnosis.

The breast CT volume data sets generally have a much better signal to noise ratio than screen film or digital mammographic images. Consequently, the application of computer algorithms to assist the radiologist or other physician in locating breast cancer (when present) is disclosed. Computer-aided diagnosis applied to breast CT data sets will likely perform better than those previously described for the evaluation of breast cancer on mammograms, due to the significantly higher signal to noise ratio of the breast CT data set. Algorithms for computer-aided detection involve assisting the radiologist (or other physician) in identifying areas in the volume data set which are suspicious and may be breast cancer.

A second class of algorithms, called computer-aided diagnosis, may be then used to perform evaluations on the specific characteristics of the shape, texture, and dimension (etc.) of the suspected area to develop a probability of abnormality or a malignancy.

14. Automatic Tracking of Normal Ductal Structures.

The breast tissues of each individual woman are unique for that woman, but ductal patterns obey similar architectural laws based upon observations of breast CT images. The ducts generally lead from the nipple then track posteriorly through the breast in linear or "warped sheet" patterns. In one embodiment, an algorithm is used to identify the normal ductal structure of a number of patients to build a database of structures that help to identify normal structures within the breast to help the diagnostician (radiologist or other physician) to rule out or better distinguish areas of suspicion.

15. Other Therapeutic Applications.

The volume data set provided by the breast CT has a high degree of spatial accuracy, and this means that other radiation and nonradiation can be applied to the breast under image guidance. Examples include the high-energy radiation beams described previously, as well as optical radiation, high-intensity focused ultrasound (HIFU) beams, and radio frequency waves which are capable of ablating the breast cancer. The benefit of these therapeutic approaches is that surgery may not be required, and the tumor itself may be completely killed under the application of such therapies.

Although the description above contains many details, these should not be construed as limiting the scope of the invention, but as merely providing illustrations of some of the presently preferred embodiments of this invention. For example, the above disclosure is directed to use in imaging the breast of the patient. However, the methods and apparatus of the present invention may be used for imaging any area of anatomy on a patient. In many cases, the volume data need not be collected by x-ray computed tomography and other forms of volume data acquisition may also be used with embodiments of the present invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public, regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method of measuring breast density, comprising:
    (a) generating a three-dimensional volume data set of at least a portion of a breast;
    (b) segmenting the three-dimensional volume data set into volume elements associated with glandular tissue and non-glandular tissue;
    (c) removing volume elements associated with skin;
    (d) calculating a volume of the portion of the breast associated with each of the glandular tissue and the non-glandular tissue; and
    (e) outputting a breast density measurement being a function of the volume of the portion of the breast associated with each of the glandular tissue and the non-glandular tissue.

2. The method as recited in claim 1, wherein segmenting the three-dimensional volume data set generates a histogram of the volume elements; and selects volume elements according to a threshold value distinguishing the glandular tissue and the non-glandular tissue.

3. The method as recited in claim 1, wherein the step of removing volume elements associated with skin applies an erosion filter to the three-dimensional volume data set.

4. The method as recited in claim 1, further comprising adjusting the breast density measurement according to a patient's age.

5. The method as recited in claim 4, further comprising the step of outputting a standard deviation of the breast density measurement with respect to patients in a particular age group.

6. The method as recited in claim 1 further including the steps of comparing the breast density measurement to data of reference patients to output a risk factor indicating a relative risk of breast cancer for an individual patient.

7. The method as recited in claim 6, wherein the comparing entails comparing the breast density measurement with a mean breast density value and a standard deviation of the mean breast density value of breast density measurements obtained from a plurality of individual reference patients grouped according to age.

8. An apparatus for measuring breast density comprising:
a table supporting a patient in a prone position with a breast;
an x-ray computed tomography (CT) scanner comprising an x-ray source and detector positioned to acquire a CT projection set about a horizontal axis around the breast; and
a computer receiving data from the x-ray computed tomography (CT) scanner programmed to:
generate a three-dimensional volume data set of at least a portion of the breast;
segment the three-dimensional volume data set into volume elements associated with glandular tissue and non-glandular tissue;
remove volume elements associated with skin;
calculate a volume of the portion of the breast associated with each of the glandular tissue and the non-glandular tissue; and
output a breast density measurement being a function of the volume of the portion of the breast associated with each of the glandular tissue and the non-glandular tissue.

9. The apparatus of claim 8, wherein segmenting the three-dimensional volume data set generates a histogram of the volume elements; and selects volume elements according to a threshold value distinguishing the glandular tissue and the non-glandular tissue.

10. The apparatus of claim 8, wherein the computer is further programmed to:
apply an erosion filter to the three-dimensional volume data set to remove the volume elements associated with skin.

11. The apparatus of claim 8, wherein the computer is further programmed to:
adjust the breast density measurement according to a patient's age.

12. The apparatus of claim 11, wherein the computer is further programmed to:
output a standard deviation of the breast density measurement with respect to patients in a particular age group.

13. The apparatus of claim 8, wherein the computer is further programmed to:
compare the breast density measurement to data of reference patients, and
output a risk factor indicating a relative risk of breast cancer for an individual patient based on the comparing.

14. The apparatus of claim 13, wherein the comparing entails comparing the breast density measurement with a mean breast density value and a standard deviation of the mean breast density value of breast density measurements obtained from a plurality of individual reference patients grouped according to age.

15. The apparatus of claim 8 further comprising:
a positron emission tomography (PET) detector positioned to acquire PET data of the breast and to transmit the data to the computer.

16. The apparatus of claim 15, wherein the three-dimensional volume data set of at least the portion of the breast is generated based on data produced by the x-ray computed tomography (CT) scanner and the PET data acquired by the PET detector.

17. A method of measuring breast density, comprising:
(a) generating a three-dimensional volume data set of at least a portion of a breast;
(b) segmenting the three-dimensional volume data set into volume elements associated with glandular tissue and non-glandular tissue;
(c) calculating a volume of the portion of the breast associated with each of the glandular tissue and the non-glandular tissue;
(d) outputting a breast density measurement being a function of the volume of the portion of the breast associated with each of the glandular tissue and the non-glandular tissue; and
(e) adjusting the breast density measurement according to a patient's age.

18. The method as recited in claim 17, wherein segmenting the three-dimensional volume data set generates a histogram of the volume elements; and selects volume elements according to a threshold value distinguishing the glandular tissue and the non-glandular tissue.

19. The method as recited in claim 17, further including the step of removing volume elements associated with skin before step (c),
wherein the step of removing volume elements associated with skin applies an erosion filter to the three-dimensional volume data set.

20. The method as recited in claim 17, further comprising the step of outputting a standard deviation of the breast density measurement with respect to patients in a particular age group.

21. The method as recited in claim 17, further including the steps of comparing the breast density measurement to data of reference patients to output a risk factor indicating a relative risk of breast cancer for an individual patient.

22. The method as recited in claim 21, wherein the comparing entails comparing the breast density measurement with a mean breast density value and a standard deviation of the mean breast density value of breast density measurements obtained from a plurality of individual reference patients grouped according to age.

23. An apparatus for measuring breast density comprising:
a table supporting a patient in a prone position with a breast;
an x-ray computed tomography (CT) scanner comprising an x-ray source and detector positioned to acquire a CT projection set about a horizontal axis around the breast; and
a computer receiving data from the x-ray computed tomography (CT) scanner programmed to:
generate a three-dimensional volume data set of at least a portion of the breast;
segment the three-dimensional volume data set into volume elements associated with glandular tissue and non-glandular tissue;
calculate a volume of the portion of the breast associated with each of the glandular tissue and the non-glandular tissue;
output a breast density measurement being a function of the volume of the portion of the breast associated with each of the glandular tissue and the non-glandular tissue; and
adjust the breast density measurement according to a patient's age.

24. The apparatus of claim 23, wherein segmenting the three-dimensional volume data set generates a histogram of the volume elements; and selects volume elements according to a threshold value distinguishing the glandular tissue and the non-glandular tissue.

25. The apparatus of claim 23, wherein the computer is further programmed to:
remove volume elements associated with skin before calculating the volume of the portion of the breast associated with each of the glandular tissue and the non-glandular tissue; and
apply an erosion filter to the three-dimensional volume data set to remove the volume elements associated with skin.

26. The apparatus of claim 23, wherein the computer is further programmed to:
output a standard deviation of the breast density measurement with respect to patients in a particular age group.

27. The apparatus of claim 23, wherein the computer is further programmed to:
compare the breast density measurement to data of reference patients, and
output a risk factor indicating a relative risk of breast cancer for an individual patient based on the comparing.

28. The apparatus of claim 27, wherein the comparing entails comparing the breast density measurement with a mean breast density value and a standard deviation of the mean breast density value of breast density measurements obtained from a plurality of individual reference patients grouped according to age.

29. The apparatus of claim 23 further comprising:
a positron emission tomography (PET) detector positioned to acquire PET data of the breast and to transmit the data to the computer.

30. The apparatus of claim 29, wherein the three-dimensional volume data set of at least the portion of the breast is generated based on data produced by the x-ray computed tomography (CT) scanner and the PET data acquired by the PET detector.

31. An apparatus for measuring breast density comprising:
a table supporting a patient in a prone position with a breast;
an x-ray computed tomography (CT) scanner comprising an x-ray source and detector positioned to acquire a CT projection set about a horizontal axis around the breast; and
a computer receiving data from the x-ray computed tomography (CT) scanner programmed to:
generate a three-dimensional volume data set of at least a portion of the breast;
segment the three-dimensional volume data set into volume elements associated with glandular tissue and non-glandular tissue;
calculate a volume of the portion of the breast associated with each of the glandular tissue and the non-glandular tissue;
output a breast density measurement being a function of the volume of the portion of the breast associated with each of the glandular tissue and the non-glandular tissue;
compare the breast density measurement to data of reference patients; and
output a risk factor indicating a relative risk of breast cancer for an individual patient based on the comparing,
wherein the comparing entails comparing the breast density measurement with a mean breast density value and a standard deviation of the mean breast density value of breast density measurements obtained from a plurality of individual reference patients grouped according to age.

32. The apparatus of claim 31, wherein segmenting the three-dimensional volume data set generates a histogram of the volume elements; and selects volume elements according to a threshold value distinguishing the glandular tissue and the non-glandular tissue.

33. The apparatus of claim 31, wherein the computer is further programmed to:
remove volume elements associated with skin before calculating the volume of the portion of the breast associated with each of the glandular tissue and the non-glandular tissue; and
apply an erosion filter to the three-dimensional volume data set to remove the volume elements associated with skin.

34. The apparatus of claim 31, wherein the computer is further programmed to:
adjust the breast density measurement according to a patient's age; and
output a standard deviation of the breast density measurement with respect to patients in a particular age group.

35. The apparatus of claim 31 further comprising:
a positron emission tomography (PET) detector positioned to acquire PET data of the breast and to transmit the data to the computer.

36. The apparatus of claim 35, wherein the three-dimensional volume data set of at least the portion of the breast is generated based on data produced by the x-ray computed tomography (CT) scanner and the PET data acquired by the PET detector.

37. A method of measuring breast density, comprising:
(a) generating a three-dimensional volume data set of at least a portion of a breast;
(b) segmenting the three-dimensional volume data set into volume elements associated with glandular tissue and non-glandular tissue;
(c) calculating a volume of the portion of the breast associated with each of the glandular tissue and the non-glandular tissue;
(d) outputting a breast density measurement being a function of the volume of the portion of the breast associated with each of the glandular tissue and the non-glandular tissue;
(e) comparing the breast density measurement to data of reference patients to output a risk factor indicating a relative risk of breast cancer for an individual patient; and
(f) outputting the risk factor indicating the relative risk of breast cancer for the individual patient based on the comparing,
wherein the comparing entails comparing the breast density measurement with a mean breast density value and a standard deviation of the mean breast density value of breast density measurements obtained from a plurality of individual reference patients grouped according to age.

38. The method as recited in claim 37, wherein segmenting the three-dimensional volume data set generates a histogram of the volume elements; and selects volume elements according to a threshold value distinguishing the glandular tissue and the non-glandular tissue.

39. The method as recited in claim 37, further including the step of removing volume elements associated with skin before step (c),
   wherein the step of removing volume elements associated with skin applies an erosion filter to the three-dimensional volume data set.

40. The method as recited in claim 37, further comprising adjusting the breast density measurement according to a patient's age.

41. The method as recited in claim 40, further comprising the step of outputting a standard deviation of the breast density measurement with respect to patients in a particular age group.

* * * * *